(12) United States Patent
Mayumi et al.

(10) Patent No.: US 7,993,636 B2
(45) Date of Patent: Aug. 9, 2011

(54) TUMOR NECROSIS FACTOR-ALPHA MUTANTS

(75) Inventors: Tadanori Mayumi, Hyogo (JP); Yasuo Tsutsumi, Osaka (JP); Shinsaku Nakagawa, Osaka (JP); Tsunetaka Ohta, Okayama (JP)

(73) Assignees: Kabushiki Kaisha Hayashibara Seibutsu Kagaku Kenkyujo, Okayama (JP); Tadanori Mayumi, Hyogo (JP); Yasuo Tstsumi, Osaka (JP); Shinsaku Nakagawa, Osaka (JP)

( * ) Notice: Subject to any disclaimer, the term of this patent is extended or adjusted under 35 U.S.C. 154(b) by 1392 days.

(21) Appl. No.: 10/585,296

(22) PCT Filed: Jan. 5, 2005

(86) PCT No.: PCT/JP2005/000032
§ 371 (c)(1),
(2), (4) Date: Jul. 6, 2006

(87) PCT Pub. No.: WO2005/066206
PCT Pub. Date: Jul. 21, 2005

(65) Prior Publication Data
US 2010/0222258 A1    Sep. 2, 2010

(30) Foreign Application Priority Data

Jan. 6, 2004 (JP) .................... 2004-001427

(51) Int. Cl.
*C07K 14/525*  (2006.01)
(52) U.S. Cl. .................. 424/85.1; 530/351; 530/402
(58) Field of Classification Search .............. None
See application file for complete search history.

(56) References Cited

U.S. PATENT DOCUMENTS 5,422,104 A    6/1995  Fiers et al.
5,486,463 A *  1/1996  Lesslauer et al. ............ 435/69.5

FOREIGN PATENT DOCUMENTS

| EP | 0247860 A2 | 12/1987 |
| EP | 0486908 A2 | 5/1992 |
| EP | 0563714 A2 | 10/1993 |
| EP | 1354893 A2 | 10/2003 |
| JP | 62-289522 | 12/1987 |
| JP | 6-256395 | 9/1994 |
| JP | 7-285997 | 10/1995 |

OTHER PUBLICATIONS

Zhang et al., Site-directed mutational analysis of human tumor necrosis factor-alpha receptor binding site and structure-functional relationship.

Van Ostade et al., Localization of the active site of human tumour necrosis factor (hTNF) by mutational analysis, *The EMBO Journal*, 10(4)827-836 (1991).

Zhang et al., Site-directed mutational analysis of human tumor necrosis factor-α receptor binding site and structure-functional relationship, *The Journal of Biological Chemistry*, 267(33)24069-24075 (1992).

Loetscher et al., Human tumor necrosis factor α (TNFα) mutants with exclusive specificity for the 55-kDa or 75 kDa TNF receptors, *The Journal of Biological Chemistry*, 268(35)26350-26357 (1993).

* cited by examiner

*Primary Examiner* — Prema Mertz
(74) *Attorney, Agent, or Firm* — Browdy and Neimark, PLLC

(57) ABSTRACT

The present invention has an object to provide a tumor necrosis factor mutant protein, particularly, a tumor necrosis factor mutant protein specific to TNF-R1 or TNF-R2; tumor necrosis factor inhibitor; or tumor necrosis factor preparation containing it as an effective ingredient, and the object is solved by providing a tumor necrosis factor mutant protein where one or more amino acid residues selected from the group consisting of 29th, 31st, 32nd, 145th, 146th and 147th, or the group consisting of 84th to 89th from the N-terminal of the amino acid sequence of SEQ ID NO:1 is/are replaced with other amino acid residue(s); a tumor necrosis factor inhibitor; and a tumor necrosis factor preparation containing it as an effective ingredient.

9 Claims, No Drawings

SEQUENCE LISTING

```
<160> NUMBER OF SEQ ID NOS: 90

<210> SEQ ID NO 1
<211> LENGTH: 157
<212> TYPE: PRT
<213> ORGANISM: Homo sapiens

<400> SEQUENCE: 1

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 2
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(471)

<400> SEQUENCE: 2 gtc aga tca tct tct cga acc ccg agt gac atg cct gta gcc cat gtt      48
Val Arg Ser Ser Ser Arg Thr Pro Ser Asp Met Pro Val Ala His Val
1               5                   10                  15 gta gca aac cct caa gct gag ggg cag ctc cag tgg ctg aac cgc cgg      96
Val Ala Asn Pro Gln Ala Glu Gly Gln Leu Gln Trp Leu Asn Arg Arg
            20                  25                  30 gcc aat gcc ctc ctg gcc aat ggc gtg gag ctg aga gat aac cag ctg      144
Ala Asn Ala Leu Leu Ala Asn Gly Val Glu Leu Arg Asp Asn Gln Leu
        35                  40                  45 gtg gtg cca tca gag ggc ctg tac ctc atc tac tcc cag gtc ctc ttc      192
Val Val Pro Ser Glu Gly Leu Tyr Leu Ile Tyr Ser Gln Val Leu Phe
    50                  55                  60 tcg ggc caa ggc tgc ccc tcc acc cat gtg ctc ctc acc cac acc atc      240
```

-continued

```
Ser Gly Gln Gly Cys Pro Ser Thr His Val Leu Leu Thr His Thr Ile
 65                  70                  75                  80 agc cgc atc gcc gtc tcc tac cag acc ccc gtc aac ctc ctc tct gcc    288
Ser Arg Ile Ala Val Ser Tyr Gln Thr Pro Val Asn Leu Leu Ser Ala
                 85                  90                  95 atc cgc agc ccc tgc cag agg gag acc cca gag ggg gct gag gcc aac    336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg    384
Pro Trp Tyr Glu Pro Ile Tyr Leu Gly Gly Val Phe Gln Leu Glu Pro
        115                 120                 125 ggt gac cga ctc agc gct gag atc aat cgg ccc gac tat ctc gac ttt    432
Gly Asp Arg Leu Ser Ala Glu Ile Asn Arg Pro Asp Tyr Leu Asp Phe
    130                 135                 140 gcc gag tct ggg cag gtc tac ttt ggg atc att gcc ctg                471
Ala Glu Ser Gly Gln Val Tyr Phe Gly Ile Ile Ala Leu
145                 150                 155
```

<210> SEQ ID NO 3
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(471)

<400> SEQUENCE: 3

```
gtc aga tca tct tct cga acc ccg agt gac gcg cct gta gcc cat gtt     48
Val Arg Ser Ser Ser Arg Thr Pro Ser Asp Ala Pro Val Ala His Val
  1               5                  10                  15 gta gca aac cct caa gct gag ggg cag ctc cag tgg ctg aac cgc cgg     96
Val Ala Asn Pro Gln Ala Glu Gly Gln Leu Gln Trp Leu Asn Arg Arg
                20                  25                  30 gcc aat gcc ctc ctg gcc aat ggc gtg gag ctg aga gat aac cag ctg    144
Ala Asn Ala Leu Leu Ala Asn Gly Val Glu Leu Arg Asp Asn Gln Leu
            35                  40                  45 gtg gtg cca tca gag ggc ctg tac ctc atc tac tcc cag gtc ctc ttc    192
Val Val Pro Ser Glu Gly Leu Tyr Leu Ile Tyr Ser Gln Val Leu Phe
        50                  55                  60 tcg ggc caa ggc tgc ccc tcc acc cat gtg ctc ctc acc cac acc atc    240
Ser Gly Gln Gly Cys Pro Ser Thr His Val Leu Leu Thr His Thr Ile
 65                  70                  75                  80 agc cgc atc gcc gtc tcc tac cag acc cgg gtc aac ctc ctc tct gcc    288
Ser Arg Ile Ala Val Ser Tyr Gln Thr Arg Val Asn Leu Leu Ser Ala
                 85                  90                  95 atc gcc agc ccc tgc cag agg gag acc cca gag ggg gct gag gcc ctc    336
Ile Ala Ser Pro Cys Gln Arg Glu Thr Pro Glu Gly Ala Glu Ala Leu
            100                 105                 110 ccc tgg tat gag ccc atc tat ctg gga ggg gtc ttc cag ctg gag acc    384
Pro Trp Tyr Glu Pro Ile Tyr Leu Gly Gly Val Phe Gln Leu Glu Thr
        115                 120                 125 ggt gac cga ctc agc gct gag atc aat cgg ccc gac tat ctc gac ttt    432
Gly Asp Arg Leu Ser Ala Glu Ile Asn Arg Pro Asp Tyr Leu Asp Phe
    130                 135                 140 gcc gag tct ggg cag gtc tac ttt ggg atc att gcc ctg                471
Ala Glu Ser Gly Gln Val Tyr Phe Gly Ile Ile Ala Leu
145                 150                 155
```

<210> SEQ ID NO 4
<211> LENGTH: 471
<212> TYPE: DNA

```
<213> ORGANISM: Artificial Sequence
<220> FEATURE:
<223> OTHER INFORMATION: Synthetic
<220> FEATURE:
<221> NAME/KEY: CDS
<222> LOCATION: (1)..(471)

<400> SEQUENCE: 4 gtc aga tca tct tct cga acc ccg agt gac gcg cct gta gcc cat gtt      48
Val Arg Ser Ser Ser Arg Thr Pro Ser Asp Ala Pro Val Ala His Val
1               5                   10                  15 gta gca aac cct caa gct gag ggg cag ctc cag tgg ctg aac cgc cgg      96
Val Ala Asn Pro Gln Ala Glu Gly Gln Leu Gln Trp Leu Asn Arg Arg
            20                  25                  30 gcc aat gcc ctc ctg gcc aat ggc gtg gag ctg aga gat aac cag ctg     144
Ala Asn Ala Leu Leu Ala Asn Gly Val Glu Leu Arg Asp Asn Gln Leu
        35                  40                  45 gtg gtg cca tca gag ggc ctg tac ctc atc tac tcc cag gtc ctc ttc     192
Val Val Pro Ser Glu Gly Leu Tyr Leu Ile Tyr Ser Gln Val Leu Phe
    50                  55                  60 tcg ggc caa ggc tgc ccc tcc acc cat gtg ctc ctc acc cac acc atc     240
Ser Gly Gln Gly Cys Pro Ser Thr His Val Leu Leu Thr His Thr Ile
65                  70                  75                  80 agc cgc atc gcc gtc tcc tac cag acc gac gtc aac ctc ctc tct gcc     288
Ser Arg Ile Ala Val Ser Tyr Gln Thr Asp Val Asn Leu Leu Ser Ala
                85                  90                  95 atc gcc agc ccc tgc cag agg gag acc cca gag ggg gct gag gcc ctc     336
Ile Ala Ser Pro Cys Gln Arg Glu Thr Pro Glu Gly Ala Glu Ala Leu
            100                 105                 110 ccc tgg tat gag ccc atc tat ctg gga ggg gtc ttc cag ctg gag acc     384
Pro Trp Tyr Glu Pro Ile Tyr Leu Gly Gly Val Phe Gln Leu Glu Thr
        115                 120                 125 ggt gac cga ctc agc gct gag atc aat cgg ccc gac tat ctc gac ttt     432
Gly Asp Arg Leu Ser Ala Glu Ile Asn Arg Pro Asp Tyr Leu Asp Phe
    130                 135                 140 gcc gag tct ggg cag gtc tac ttt ggg atc att gcc ctg                 471
Ala Glu Ser Gly Gln Val Tyr Phe Gly Ile Ile Ala Leu
145                 150                 155

<210> SEQ ID NO 5
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (145)..(147)
<223> OTHER INFORMATION: Xaa can be any naturally occurring amino acid

<400> SEQUENCE: 5

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Xaa Asn Xaa Xaa
            20                  25                  30

Ala Asn Ala Leu Leu Ala Asn Gly Val Glu Leu Arg Asp Asn Gln Leu
        35                  40                  45
```

```
Val Val Pro Ser Glu Gly Leu Tyr Leu Ile Tyr Ser Gln Val Leu Phe
 50                  55                  60

Ser Gly Gln Gly Cys Pro Ser Thr His Val Leu Thr His Thr Ile
 65                  70                  75                  80

Ser Arg Ile Ala Val Ser Tyr Gln Thr Pro Val Asn Leu Leu Ser Ala
                 85                  90                  95

Ile Arg Ser Pro Cys Gln Arg Glu Thr Pro Glu Gly Ala Glu Ala Asn
             100                 105                 110

Pro Trp Tyr Glu Pro Ile Tyr Leu Gly Gly Val Phe Gln Leu Glu Pro
             115                 120             125

Gly Asp Arg Leu Ser Ala Glu Ile Asn Arg Pro Asp Tyr Leu Asp Phe
         130                 135                 140

Xaa Xaa Xaa Gly Gln Val Tyr Phe Gly Ile Ile Ala Leu
145                 150                 155
```

<210> SEQ ID NO 6
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(471)
<220> FEATURE:
<221> NAME/KEY: misc_feature
<222> LOCATION: (85)..(86)
<223> OTHER INFORMATION: n is a, c, g, or t
<220> FEATURE:
<221> NAME/KEY: misc_feature
<222> LOCATION: (91)..(92)
<223> OTHER INFORMATION: n is a, c, g, or t
<220> FEATURE:
<221> NAME/KEY: misc_feature
<222> LOCATION: (94)..(95)
<223> OTHER INFORMATION: n is a, c, g, or t
<220> FEATURE:
<221> NAME/KEY: misc_feature
<222> LOCATION: (433)..(434)
<223> OTHER INFORMATION: n is a, c, g, or t
<220> FEATURE:
<221> NAME/KEY: misc_feature
<222> LOCATION: (436)..(437)
<223> OTHER INFORMATION: n is a, c, g, or t
<220> FEATURE:
<221> NAME/KEY: misc_feature
<222> LOCATION: (439)..(440)
<223> OTHER INFORMATION: n is a, c, g, or t

<400> SEQUENCE: 6

```
gtc aga tca tct tct cga acc ccg agt gac atg cct gta gcc cat gtt      48
Val Arg Ser Ser Ser Arg Thr Pro Ser Asp Met Pro Val Ala His Val
 1               5                  10                  15 gta gca aac cct caa gct gag ggg cag ctc cag tgg nns aac nns nns      96
Val Ala Asn Pro Gln Ala Glu Gly Gln Leu Gln Trp Xaa Asn Xaa Xaa
                 20                  25                  30 gcc aat gcc ctc ctg gcc aat ggc gtg gag ctg aga gat aac cag ctg     144
Ala Asn Ala Leu Leu Ala Asn Gly Val Glu Leu Arg Asp Asn Gln Leu
             35                  40                  45 gtg gtg cca tca gag ggc ctg tac ctc atc tac tcc cag gtc ctc ttc     192
Val Val Pro Ser Glu Gly Leu Tyr Leu Ile Tyr Ser Gln Val Leu Phe
 50                  55                  60 tcg ggc caa ggc tgc ccc tcc acc cat gtg ctc ctc acc cac acc atc     240
Ser Gly Gln Gly Cys Pro Ser Thr His Val Leu Leu Thr His Thr Ile
 65                  70                  75                  80 agc cgc atc gcc gtc tcc tac cag acc ccc gtc aac ctc ctc tct gcc     288
Ser Arg Ile Ala Val Ser Tyr Gln Thr Pro Val Asn Leu Leu Ser Ala
```

```
                              85                  90                  95
atc cgc agc ccc tgc cag agg gag acc cca gag ggg gct gag gcc aac      336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg      384
Pro Trp Tyr Glu Pro Ile Tyr Leu Gly Gly Val Phe Gln Leu Glu Pro
                115                 120                 125 ggt gac cga ctc agc gct gag atc aat cgg ccc gac tat ctc gac ttt      432
Gly Asp Arg Leu Ser Ala Glu Ile Asn Arg Pro Asp Tyr Leu Asp Phe
130                 135                 140 nns nns nns ggg cag gtc tac ttt ggg atc att gcc ctg                  471
Xaa Xaa Xaa Gly Gln Val Tyr Phe Gly Ile Ile Ala Leu
145                 150                 155

<210> SEQ ID NO 7
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (84)..(89)
<223> OTHER INFORMATION: Xaa can be any naturally occurring amino acid

<400> SEQUENCE: 7

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
        50                  55                  60

Ser Gly Gln Gly Cys Pro Ser Thr His Val Leu Leu Thr His Thr Ile
65                  70                  75                  80

Ser Arg Ile Xaa Xaa Xaa Xaa Xaa Xaa Pro Val Asn Leu Leu Ser Ala
                85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
        115                 120                 125

Gly Asp Arg Leu Ser Ala Glu Ile Asn Arg Pro Asp Tyr Leu Asp Phe
130                 135                 140

Ala Glu Ser Gly Gln Val Tyr Phe Gly Ile Ile Ala Leu
145                 150                 155

<210> SEQ ID NO 8
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(471)
<220> FEATURE:
<221> NAME/KEY: misc_feature
<222> LOCATION: (250)..(251)
<223> OTHER INFORMATION: n is a, c, g, or t
<220> FEATURE:
<221> NAME/KEY: misc_feature
<222> LOCATION: (253)..(254)
<223> OTHER INFORMATION: n is a, c, g, or t
```

```
<220> FEATURE:
<221> NAME/KEY: misc_feature
<222> LOCATION: (256)..(257)
<223> OTHER INFORMATION: n is a, c, g, or t
<220> FEATURE:
<221> NAME/KEY: misc_feature
<222> LOCATION: (259)..(260)
<223> OTHER INFORMATION: n is a, c, g, or t
<220> FEATURE:
<221> NAME/KEY: misc_feature
<222> LOCATION: (262)..(263)
<223> OTHER INFORMATION: n is a, c, g, or t
<220> FEATURE:
<221> NAME/KEY: misc_feature
<222> LOCATION: (265)..(266)
<223> OTHER INFORMATION: n is a, c, g, or t

<400> SEQUENCE: 8 gtc aga tca tct tct cga acc ccg agt gac atg cct gta gcc cat gtt      48
Val Arg Ser Ser Ser Arg Thr Pro Ser Asp Met Pro Val Ala His Val
1               5                   10                  15 gta gca aac cct caa gct gag ggg cag ctc cag tgg ctg aac cgc cgg      96
Val Ala Asn Pro Gln Ala Glu Gly Gln Leu Gln Trp Leu Asn Arg Arg
            20                  25                  30 gcc aat gcc ctc ctg gcc aat ggc gtg gag ctg aga gat aac cag ctg     144
Ala Asn Ala Leu Leu Ala Asn Gly Val Glu Leu Arg Asp Asn Gln Leu
        35                  40                  45 gtg gtg cca tca gag ggc ctg tac ctc atc tac tcc cag gtc ctc ttc     192
Val Val Pro Ser Glu Gly Leu Tyr Leu Ile Tyr Ser Gln Val Leu Phe
    50                  55                  60 tcg ggc caa ggc tgc ccc tcc acc cat gtg ctc ctc acc cac acc atc     240
Ser Gly Gln Gly Cys Pro Ser Thr His Val Leu Leu Thr His Thr Ile
65                  70                  75                  80 agc cgc atc nns nns nns nns nns nns ccc gtc aac ctc ctc tct gcc     288
Ser Arg Ile Xaa Xaa Xaa Xaa Xaa Xaa Pro Val Asn Leu Leu Ser Ala
                85                  90                  95 atc cgc agc ccc tgc cag agg gag acc cca gag ggg gct gag gcc aac     336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg     384
Pro Trp Tyr Glu Pro Ile Tyr Leu Gly Gly Val Phe Gln Leu Glu Pro
        115                 120                 125 ggt gac cga ctc agc gct gag atc aat cgg ccc gac tat ctc gac ttt     432
Gly Asp Arg Leu Ser Ala Glu Ile Asn Arg Pro Asp Tyr Leu Asp Phe
    130                 135                 140 gcc gag tct ggg cag gtc tac ttt ggg atc att gcc ctg                 471
Ala Glu Ser Gly Gln Val Tyr Phe Gly Ile Ile Ala Leu
145                 150                 155

<210> SEQ ID NO 9
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 5

<400> SEQUENCE: 9

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Arg Asn Ser His
            20                  25                  30

Ala Asn Ala Leu Leu Ala Asn Gly Val Glu Leu Arg Asp Asn Gln Leu
        35                  40                  45
```

Val Val Pro Ser Glu Gly Leu Tyr Leu Ile Tyr Ser Gln Val Leu Phe
                50                  55                  60

Ser Gly Gln Gly Cys Pro Ser Thr His Val Leu Leu Thr His Thr Ile
65                  70                  75                  80

Ser Arg Ile Ala Val Ser Tyr Gln Thr Pro Val Asn Leu Leu Ser Ala
                85                  90                  95

Ile Arg Ser Pro Cys Gln Arg Glu Thr Pro Glu Gly Ala Glu Ala Asn
                100                 105                 110

Pro Trp Tyr Glu Pro Ile Tyr Leu Gly Gly Val Phe Gln Leu Glu Pro
                115                 120                 125

Gly Asp Arg Leu Ser Ala Glu Ile Asn Arg Pro Asp Tyr Leu Asp Phe
    130                 135                 140

Ser Gly Thr Gly Gln Val Tyr Phe Gly Ile Ile Ala Leu
145                 150                 155

<210> SEQ ID NO 10
<211> LENGTH: 146
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 6

<400> SEQUENCE: 10

Val Arg Ser Ser Arg Thr Pro Ser Asp Met Pro Val Ala His Val
1               5                   10                  15

Val Ala Asn Pro Gln Ala Glu Gly Gln Leu Gln Trp Ser Asn Arg Tyr
                20                  25                  30

Ala Asn Ala Leu Leu Ala Asn Gly Val Glu Leu Arg Asp Asn Gln Leu
                35                  40                  45

Val Val Pro Ser Glu Gly Leu Tyr Leu Ile Tyr Ser Gln Val Leu Phe
                50                  55                  60

Ser Gly Gln Gly Cys Pro Ser Thr His Val Leu Leu Thr His Thr Ile
65                  70                  75                  80

Ser Arg Ile Ala Val Ser Tyr Gln Thr Pro Val Asn Leu Leu Ser Ala
                85                  90                  95

Ile Arg Ser Pro Cys Gln Arg Glu Thr Pro Glu Gly Ala Glu Ala Asn
                100                 105                 110

Pro Trp Tyr Glu Pro Ile Tyr Leu Gly Gly Val Phe Gln Leu Glu Pro
                115                 120                 125

Gly Asp Arg Leu Ser Ala Glu Ile Asn Arg Pro Asp Tyr Leu Asp Phe
    130                 135                 140

Ser Met
145

<210> SEQ ID NO 11
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 7

<400> SEQUENCE: 11

Val Arg Ser Ser Arg Thr Pro Ser Asp Met Pro Val Ala His Val
1               5                   10                  15

```
Val Ala Asn Pro Gln Ala Glu Gly Gln Leu Gln Trp His Asn Asn Thr
             20                  25                  30

Ala Asn Ala Leu Leu Ala Asn Gly Val Glu Leu Arg Asp Asn Gln Leu
         35                  40                  45

Val Val Pro Ser Glu Gly Leu Tyr Leu Ile Tyr Ser Gln Val Leu Phe
     50                  55                  60

Ser Gly Gln Gly Cys Pro Ser Thr His Val Leu Leu Thr His Thr Ile
65                  70                  75                  80

Ser Arg Ile Ala Val Ser Tyr Gln Thr Pro Val Asn Leu Leu Ser Ala
                 85                  90                  95

Ile Arg Ser Pro Cys Gln Arg Glu Thr Pro Glu Gly Ala Glu Ala Asn
                100                 105                 110

Pro Trp Tyr Glu Pro Ile Tyr Leu Gly Gly Val Phe Gln Leu Glu Pro
            115                 120                 125

Gly Asp Arg Leu Ser Ala Glu Ile Asn Arg Pro Asp Tyr Leu Asp Phe
130                 135                 140

Asp Ser Asn Gly Gln Val Tyr Phe Gly Ile Ile Ala Leu
145                 150                 155
```

```
<210> SEQ ID NO 12
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 8

<400> SEQUENCE: 12
```

```
Val Arg Ser Ser Ser Arg Thr Pro Ser Asp Met Pro Val Ala His Val
1               5                   10                  15

Val Ala Asn Pro Gln Ala Glu Gly Gln Leu Gln Trp Arg Asn Glu His
             20                  25                  30

Ala Asn Ala Leu Leu Ala Asn Gly Val Glu Leu Arg Asp Asn Gln Leu
         35                  40                  45

Val Val Pro Ser Glu Gly Leu Tyr Leu Ile Tyr Ser Gln Val Leu Phe
     50                  55                  60

Ser Gly Gln Gly Cys Pro Ser Thr His Val Leu Leu Thr His Thr Ile
65                  70                  75                  80

Ser Arg Ile Ala Val Ser Tyr Gln Thr Pro Val Asn Leu Leu Ser Ala
                 85                  90                  95

Ile Arg Ser Pro Cys Gln Arg Glu Thr Pro Glu Gly Ala Glu Ala Asn
                100                 105                 110

Pro Trp Tyr Glu Pro Ile Tyr Leu Gly Gly Val Phe Gln Leu Glu Pro
            115                 120                 125

Gly Asp Arg Leu Ser Ala Glu Ile Asn Arg Pro Asp Tyr Leu Asp Phe
130                 135                 140

Asn Asn Ala Gly Gln Val Tyr Phe Gly Ile Ile Ala Leu
145                 150                 155
```

```
<210> SEQ ID NO 13
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
```

<223> OTHER INFORMATION: Clone No.9

<400> SEQUENCE: 13

```
Val Arg Ser Ser Ser Arg Thr Pro Ser Asp Met Pro Val Ala His Val
1               5                   10                  15

Val Ala Asn Pro Gln Ala Glu Gly Gln Leu Gln Trp Ser Asn Pro Met
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
65                  70                  75                  80

Ser Arg Ile Ala Val Ser Tyr Gln Thr Pro Val Asn Leu Leu Ser Ala
                85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
        115                 120                 125

Gly Asp Arg Leu Ser Ala Glu Ile Asn Arg Pro Asp Tyr Leu Asp Phe
    130                 135                 140

Ala Asn Pro Gly Gln Val Tyr Phe Gly Ile Ile Ala Leu
145                 150                 155
```

<210> SEQ ID NO 14
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 10

<400> SEQUENCE: 14

```
Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
65                  70                  75                  80

Ser Arg Ile Ala Val Ser Tyr Gln Thr Pro Val Asn Leu Leu Ser Ala
                85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
        115                 120                 125

Gly Asp Arg Leu Ser Ala Glu Ile Asn Arg Pro Asp Tyr Leu Asp Phe
    130                 135                 140

Lys Asp Thr Gly Gln Val Tyr Phe Gly Ile Ile Ala Leu
145                 150                 155
```

<210> SEQ ID NO 15
<211> LENGTH: 157

```
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 11

<400> SEQUENCE: 15

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
        50                  55                  60

Ser Gly Gln Gly Cys Pro Ser Thr His Val Leu Leu Thr His Thr Ile
65                  70                  75                  80

Ser Arg Ile Ala Val Ser Tyr Gln Thr Pro Val Asn Leu Leu Ser Ala
                85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
        115                 120                 125

Gly Asp Arg Leu Ser Ala Glu Ile Asn Arg Pro Asp Tyr Leu Asp Phe
    130                 135                 140

Arg Thr Asp Gly Gln Val Tyr Phe Gly Ile Ile Ala Leu
145                 150                 155

<210> SEQ ID NO 16
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 12

<400> SEQUENCE: 16

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
        50                  55                  60

Ser Gly Gln Gly Cys Pro Ser Thr His Val Leu Leu Thr His Thr Ile
65                  70                  75                  80

Ser Arg Ile Ala Val Ser Tyr Gln Thr Pro Val Asn Leu Leu Ser Ala
                85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
        115                 120                 125

Gly Asp Arg Leu Ser Ala Glu Ile Asn Arg Pro Asp Tyr Leu Asp Phe
    130                 135                 140
```

Arg Glu Thr Gly Gln Val Tyr Phe Gly Ile Ile Ala Leu
145                 150                 155

<210> SEQ ID NO 17
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 13

<400> SEQUENCE: 17

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
65                  70                  75                  80

Ser Arg Ile Ala Val Ser Tyr Gln Thr Pro Val Asn Leu Leu Ser Ala
                85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
        115                 120                 125

Gly Asp Arg Leu Ser Ala Glu Ile Asn Arg Pro Asp Tyr Leu Asp Phe
    130                 135                 140

Ala Asp Asp Gly Gln Val Tyr Phe Gly Ile Ile Ala Leu
145                 150                 155

<210> SEQ ID NO 18
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 14

<400> SEQUENCE: 18

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
65                  70                  75                  80

Ser Arg Ile Ala Val Ser Tyr Gln Thr Pro Val Asn Leu Leu Ser Ala
                85                  90                  95

Ile Arg Ser Pro Cys Gln Arg Glu Thr Pro Glu Gly Ala Glu Ala Asn
            100                 105                 110

```
Pro Trp Tyr Glu Pro Ile Tyr Leu Gly Gly Val Phe Gln Leu Glu Pro
            115                 120                 125

Gly Asp Arg Leu Ser Ala Glu Ile Asn Arg Pro Tyr Leu Asp Phe
            130                 135                 140

Ala Asn Asp Gly Gln Val Tyr Phe Gly Ile Ile Ala Leu
145                 150                 155
```

<210> SEQ ID NO 19
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 35

<400> SEQUENCE: 19

```
Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
65                  70                  75                  80

Ser Arg Ile Thr Pro Ala Ile Asn Arg Pro Val Asn Leu Leu Ser Ala
                85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155
```

<210> SEQ ID NO 20
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 36

<400> SEQUENCE: 20

```
Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
65                  70                  75                  80
```

-continued

Ser Arg Ile Ala Pro Gly Tyr Ser His Pro Val Asn Leu Leu Ser Ala
                85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 21
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 37

<400> SEQUENCE: 21

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
65                  70                  75                  80

Ser Arg Ile Ser Thr Thr His Asn Gln Pro Val Asn Leu Leu Ser Ala
                85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 22
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 38

<400> SEQUENCE: 22

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

```
Val Val Pro Ser Glu Gly Leu Tyr Leu Ile Tyr Ser Gln Val Leu Phe
        50                  55                  60

Ser Gly Gln Gly Cys Pro Ser Thr His Val Leu Leu Thr His Thr Ile
65                  70                  75                  80

Ser Arg Ile Gly Gly Pro Tyr Gln Arg Pro Val Asn Leu Leu Ser Ala
                85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155
```

```
<210> SEQ ID NO 23
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 5
<220> FEATURE:
<221> NAME/KEY: CDS
<222> LOCATION: (1)..(471)

<400> SEQUENCE: 23 gtc aga tca tct tct cga acc ccg agt gac atg cct gta gcc cat gtt     48
Val Arg Ser Ser Ser Arg Thr Pro Ser Asp Met Pro Val Ala His Val
1               5                   10                  15 gta gca aac cct caa gct gag ggg cag ctc cag tgg agg aac tcg cac     96
Val Ala Asn Pro Gln Ala Glu Gly Gln Leu Gln Trp Arg Asn Ser His
            20                  25                  30 gcc aat gcc ctc ctg gcc aat ggc gtg gag ctg aga gat aac cag ctg    144
Ala Asn Ala Leu Leu Ala Asn Gly Val Glu Leu Arg Asp Asn Gln Leu
        35                  40                  45 gtg gtg cca tca gag ggc ctg tac ctc atc tac tcc cag gtc ctc ttc    192
Val Val Pro Ser Glu Gly Leu Tyr Leu Ile Tyr Ser Gln Val Leu Phe
    50                  55                  60 tcg ggc caa ggc tgc ccc tcc acc cat gtg ctc ctc acc cac acc atc    240
Ser Gly Gln Gly Cys Pro Ser Thr His Val Leu Leu Thr His Thr Ile
65                  70                  75                  80 agc cgc atc gcc gtc tcc tac cag acc ccc gtc aac ctc ctc tct gcc    288
Ser Arg Ile Ala Val Ser Tyr Gln Thr Pro Val Asn Leu Leu Ser Ala
                85                  90                  95 atc cgc agc ccc tgc cag agg gag acc cca gag ggg gct gag gcc aac    336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg    384
Pro Trp Tyr Glu Pro Ile Tyr Leu Gly Gly Val Phe Gln Leu Glu Pro
        115                 120                 125 ggt gac cga ctc agc gct gag atc aat cgg ccc gac tat ctc gac ttt    432
Gly Asp Arg Leu Ser Ala Glu Ile Asn Arg Pro Asp Tyr Leu Asp Phe
    130                 135                 140 tcg ggc acc ggg cag gtc tac ttt ggg atc att gcc ctg                471
Ser Gly Thr Gly Gln Val Tyr Phe Gly Ile Ile Ala Leu
145                 150                 155

<210> SEQ ID NO 24
<211> LENGTH: 441
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 6
<220> FEATURE:
<221> NAME/KEY: CDS
<222> LOCATION: (1)..(441)

<400> SEQUENCE: 24 gtc aga tca tct tct cga acc ccg agt gac atg cct gta gcc cat gtt     48
Val Arg Ser Ser Ser Arg Thr Pro Ser Asp Met Pro Val Ala His Val
 1               5                  10                  15 gta gca aac cct caa gct gag ggg cag ctc cag tgg tcg aac cgg tac     96
Val Ala Asn Pro Gln Ala Glu Gly Gln Leu Gln Trp Ser Asn Arg Tyr
             20                  25                  30 gcc aat gcc ctc ctg gcc aat ggc gtg gag ctg aga gat aac cag ctg    144
Ala Asn Ala Leu Leu Ala Asn Gly Val Glu Leu Arg Asp Asn Gln Leu
         35                  40                  45 gtg gtg cca tca gag ggc ctg tac ctc atc tac tcc cag gtc ctc ttc    192
Val Val Pro Ser Glu Gly Leu Tyr Leu Ile Tyr Ser Gln Val Leu Phe
     50                  55                  60 tcg ggc caa ggc tgc ccc tcc acc cat gtg ctc ctc acc cac acc atc    240
Ser Gly Gln Gly Cys Pro Ser Thr His Val Leu Leu Thr His Thr Ile
 65                  70                  75                  80 agc cgc atc gcc gtc tcc tac cag acc ccc gtc aac ctc ctc tct gcc    288
Ser Arg Ile Ala Val Ser Tyr Gln Thr Pro Val Asn Leu Leu Ser Ala
                 85                  90                  95 atc cgc agc ccc tgc cag agg gag acc cca gag ggg gct gag gcc aac    336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg    384
Pro Trp Tyr Glu Pro Ile Tyr Leu Gly Gly Val Phe Gln Leu Glu Pro
        115                 120                 125 ggt gac cga ctc agc gct gag atc aat cgg ccc gac tat ctc gac ttt    432
Gly Asp Arg Leu Ser Ala Glu Ile Asn Arg Pro Asp Tyr Leu Asp Phe
    130                 135                 140 tcc atg tag                                                        441
Ser Met
145

<210> SEQ ID NO 25
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 7
<220> FEATURE:
<221> NAME/KEY: CDS
<222> LOCATION: (1)..(471)

<400> SEQUENCE: 25 gtc aga tca tct tct cga acc ccg agt gac atg cct gta gcc cat gtt     48
Val Arg Ser Ser Ser Arg Thr Pro Ser Asp Met Pro Val Ala His Val
 1               5                  10                  15 gta gca aac cct caa gct gag ggg cag ctc cag tgg cac aac aac acg     96
Val Ala Asn Pro Gln Ala Glu Gly Gln Leu Gln Trp His Asn Asn Thr
             20                  25                  30 gcc aat gcc ctc ctg gcc aat ggc gtg gag ctg aga gat aac cag ctg    144
Ala Asn Ala Leu Leu Ala Asn Gly Val Glu Leu Arg Asp Asn Gln Leu
         35                  40                  45
```

```
gtg gtg cca tca gag ggc ctg tac ctc atc tac tcc cag gtc ctc ttc      192
Val Val Pro Ser Glu Gly Leu Tyr Leu Ile Tyr Ser Gln Val Leu Phe
 50                  55                  60 tcg ggc caa ggc tgc ccc tcc acc cat gtg ctc ctc acc cac acc atc      240
Ser Gly Gln Gly Cys Pro Ser Thr His Val Leu Leu Thr His Thr Ile
 65                  70                  75                  80 agc cgc atc gcc gtc tcc tac cag acc ccc gtc aac ctc ctc tct gcc      288
Ser Arg Ile Ala Val Ser Tyr Gln Thr Pro Val Asn Leu Leu Ser Ala
                 85                  90                  95 atc cgc agc ccc tgc cag agg gag acc cca gag ggg gct gag gcc aac      336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg      384
Pro Trp Tyr Glu Pro Ile Tyr Leu Gly Gly Val Phe Gln Leu Glu Pro
            115                 120                 125 ggt gac cga ctc agc gct gag atc aat cgg ccc gac tat ctc gac ttt      432
Gly Asp Arg Leu Ser Ala Glu Ile Asn Arg Pro Asp Tyr Leu Asp Phe
130                 135                 140 gac tcc aac ggg cag gtc tac ttt ggg atc att gcc ctg                  471
Asp Ser Asn Gly Gln Val Tyr Phe Gly Ile Ile Ala Leu
145                 150                 155

<210> SEQ ID NO 26
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 8
<220> FEATURE:
<221> NAME/KEY: CDS
<222> LOCATION: (1)..(471)

<400> SEQUENCE: 26 gtc aga tca tct tct cga acc ccg agt gac atg cct gta gcc cat gtt      48
Val Arg Ser Ser Ser Arg Thr Pro Ser Asp Met Pro Val Ala His Val
 1               5                  10                  15 gta gca aac cct caa gct gag ggg cag ctc cag tgg cgc aac gag cac      96
Val Ala Asn Pro Gln Ala Glu Gly Gln Leu Gln Trp Arg Asn Glu His
             20                  25                  30 gcc aat gcc ctc ctg gcc aat ggc gtg gag ctg aga gat aac cag ctg      144
Ala Asn Ala Leu Leu Ala Asn Gly Val Glu Leu Arg Asp Asn Gln Leu
         35                  40                  45 gtg gtg cca tca gag ggc ctg tac ctc atc tac tcc cag gtc ctc ttc      192
Val Val Pro Ser Glu Gly Leu Tyr Leu Ile Tyr Ser Gln Val Leu Phe
 50                  55                  60 tcg ggc caa ggc tgc ccc tcc acc cat gtg ctc ctc acc cac acc atc      240
Ser Gly Gln Gly Cys Pro Ser Thr His Val Leu Leu Thr His Thr Ile
 65                  70                  75                  80 agc cgc atc gcc gtc tcc tac cag acc ccc gtc aac ctc ctc tct gcc      288
Ser Arg Ile Ala Val Ser Tyr Gln Thr Pro Val Asn Leu Leu Ser Ala
                 85                  90                  95 atc cgc agc ccc tgc cag agg gag acc cca gag ggg gct gag gcc aac      336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg      384
Pro Trp Tyr Glu Pro Ile Tyr Leu Gly Gly Val Phe Gln Leu Glu Pro
            115                 120                 125 ggt gac cga ctc agc gct gag atc aat cgg ccc gac tat ctc gac ttt      432
Gly Asp Arg Leu Ser Ala Glu Ile Asn Arg Pro Asp Tyr Leu Asp Phe
130                 135                 140
```

```
aac aac gcg ggg cag gtc tac ttt ggg atc att gcc ctg                471
Asn Asn Ala Gly Gln Val Tyr Phe Gly Ile Ile Ala Leu
145                 150                 155
```

```
<210> SEQ ID NO 27
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 9
<220> FEATURE:
<221> NAME/KEY: CDS
<222> LOCATION: (1)..(471)

<400> SEQUENCE: 27
```

```
gtc aga tca tct tct cga acc ccg agt gac atg cct gta gcc cat gtt     48
Val Arg Ser Ser Ser Arg Thr Pro Ser Asp Met Pro Val Ala His Val
1               5                   10                  15 gta gca aac cct caa gct gag ggg cag ctc cag tgg agc aac ccc atg     96
Val Ala Asn Pro Gln Ala Glu Gly Gln Leu Gln Trp Ser Asn Pro Met
                20                  25                  30 gcc aat gcc ctc ctg gcc aat ggc gtg gag ctg aga gat aac cag ctg    144
Ala Asn Ala Leu Leu Ala Asn Gly Val Glu Leu Arg Asp Asn Gln Leu
            35                  40                  45 gtg gtg cca tca gag ggc ctg tac ctc atc tac tcc cag gtc ctc ttc    192
Val Val Pro Ser Glu Gly Leu Tyr Leu Ile Tyr Ser Gln Val Leu Phe
50                  55                  60 tcg ggc caa ggc tgc ccc tcc acc cat gtg ctc ctc acc cac acc atc    240
Ser Gly Gln Gly Cys Pro Ser Thr His Val Leu Leu Thr His Thr Ile
65                  70                  75                  80 agc cgc atc gcc gtc tcc tac cag acc ccc gtc aac ctc ctc tct gcc    288
Ser Arg Ile Ala Val Ser Tyr Gln Thr Pro Val Asn Leu Leu Ser Ala
                85                  90                  95 atc cgc agc ccc tgc cag agg gag acc cca gag ggg gct gag gcc aac    336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg    384
Pro Trp Tyr Glu Pro Ile Tyr Leu Gly Gly Val Phe Gln Leu Glu Pro
        115                 120                 125 ggt gac cga ctc agc gct gag atc aat cgg ccc gac tat ctc gac ttt    432
Gly Asp Arg Leu Ser Ala Glu Ile Asn Arg Pro Asp Tyr Leu Asp Phe
130                 135                 140 gcc aac ccc ggg cag gtc tac ttt ggg atc att gcc ctg                471
Ala Asn Pro Gly Gln Val Tyr Phe Gly Ile Ile Ala Leu
145                 150                 155
```

```
<210> SEQ ID NO 28
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 10
<220> FEATURE:
<221> NAME/KEY: CDS
<222> LOCATION: (1)..(471)

<400> SEQUENCE: 28
```

```
gtc aga tca tct tct cga acc ccg agt gac atg cct gta gcc cat gtt     48
Val Arg Ser Ser Ser Arg Thr Pro Ser Asp Met Pro Val Ala His Val
1               5                   10                  15
```

```
gta gca aac cct caa gct gag ggg cag ctc cag tgg ctg aac cgc cgg      96
Val Ala Asn Pro Gln Ala Glu Gly Gln Leu Gln Trp Leu Asn Arg Arg
         20                  25                  30 gcc aat gcc ctc ctg gcc aat ggc gtg gag ctg aga gat aac cag ctg     144
Ala Asn Ala Leu Leu Ala Asn Gly Val Glu Leu Arg Asp Asn Gln Leu
     35                  40                  45 gtg gtg cca tca gag ggc ctg tac ctc atc tac tcc cag gtc ctc ttc     192
Val Val Pro Ser Glu Gly Leu Tyr Leu Ile Tyr Ser Gln Val Leu Phe
 50                  55                  60 tcg ggc caa ggc tgc ccc tcc acc cat gtg ctc ctc acc cac acc atc     240
Ser Gly Gln Gly Cys Pro Ser Thr His Val Leu Leu Thr His Thr Ile
 65                  70                  75                  80 agc cgc atc gcc gtc tcc tac cag acc ccc gtc aac ctc ctc tct gcc     288
Ser Arg Ile Ala Val Ser Tyr Gln Thr Pro Val Asn Leu Leu Ser Ala
             85                  90                  95 atc cgc agc ccc tgc cag agg gag acc cca gag ggg gct gag gcc aac     336
Ile Arg Ser Pro Cys Gln Arg Glu Thr Pro Glu Gly Ala Glu Ala Asn
         100                 105                 110 ccc tgg tat gag ccc atc tat ctg gga ggg gtc ttc cag ctg gag ccg     384
Pro Trp Tyr Glu Pro Ile Tyr Leu Gly Gly Val Phe Gln Leu Glu Pro
     115                 120                 125 ggt gac cga ctc agc gct gag atc aat cgg ccc gac tat ctc gac ttt     432
Gly Asp Arg Leu Ser Ala Glu Ile Asn Arg Pro Asp Tyr Leu Asp Phe
 130                 135                 140 aag gac acg ggg cag gtc tac ttt ggg atc att gcc ctg                 471
Lys Asp Thr Gly Gln Val Tyr Phe Gly Ile Ile Ala Leu
 145                 150                 155

<210> SEQ ID NO 29
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 11
<220> FEATURE:
<221> NAME/KEY: CDS
<222> LOCATION: (1)..(471)

<400> SEQUENCE: 29 gtc aga tca tct tct cga acc ccg agt gac atg cct gta gcc cat gtt      48
Val Arg Ser Ser Ser Arg Thr Pro Ser Asp Met Pro Val Ala His Val
 1               5                  10                  15 gta gca aac cct caa gct gag ggg cag ctc cag tgg ctg aac cgc cgg      96
Val Ala Asn Pro Gln Ala Glu Gly Gln Leu Gln Trp Leu Asn Arg Arg
             20                  25                  30 gcc aat gcc ctc ctg gcc aat ggc gtg gag ctg aga gat aac cag ctg     144
Ala Asn Ala Leu Leu Ala Asn Gly Val Glu Leu Arg Asp Asn Gln Leu
         35                  40                  45 gtg gtg cca tca gag ggc ctg tac ctc atc tac tcc cag gtc ctc ttc     192
Val Val Pro Ser Glu Gly Leu Tyr Leu Ile Tyr Ser Gln Val Leu Phe
     50                  55                  60 tcg ggc caa ggc tgc ccc tcc acc cat gtg ctc ctc acc cac acc atc     240
Ser Gly Gln Gly Cys Pro Ser Thr His Val Leu Leu Thr His Thr Ile
 65                  70                  75                  80 agc cgc atc gcc gtc tcc tac cag acc ccc gtc aac ctc ctc tct gcc     288
Ser Arg Ile Ala Val Ser Tyr Gln Thr Pro Val Asn Leu Leu Ser Ala
                 85                  90                  95 atc cgc agc ccc tgc cag agg gag acc cca gag ggg gct gag gcc aac     336
Ile Arg Ser Pro Cys Gln Arg Glu Thr Pro Glu Gly Ala Glu Ala Asn
             100                 105                 110
```

```
ccc tgg tat gag ccc atc tat ctg gga ggg gtc ttc cag ctg gag ccg      384
Pro Trp Tyr Glu Pro Ile Tyr Leu Gly Gly Val Phe Gln Leu Glu Pro
        115                 120                 125 ggt gac cga ctc agc gct gag atc aat cgg ccc gac tat ctc gac ttt      432
Gly Asp Arg Leu Ser Ala Glu Ile Asn Arg Pro Asp Tyr Leu Asp Phe
130                 135                 140 cgg acg gac ggg cag gtc tac ttt ggg atc att gcc ctg                  471
Arg Thr Asp Gly Gln Val Tyr Phe Gly Ile Ile Ala Leu
145                 150                 155

<210> SEQ ID NO 30
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 12
<220> FEATURE:
<221> NAME/KEY: CDS
<222> LOCATION: (1)..(471)

<400> SEQUENCE: 30 gtc aga tca tct tct cga acc ccg agt gac atg cct gta gcc cat gtt      48
Val Arg Ser Ser Ser Arg Thr Pro Ser Asp Met Pro Val Ala His Val
1               5                   10                  15 gta gca aac cct caa gct gag ggg cag ctc cag tgg ctg aac cgc cgg      96
Val Ala Asn Pro Gln Ala Glu Gly Gln Leu Gln Trp Leu Asn Arg Arg
            20                  25                  30 gcc aat gcc ctc ctg gcc aat ggc gtg gag ctg aga gat aac cag ctg      144
Ala Asn Ala Leu Leu Ala Asn Gly Val Glu Leu Arg Asp Asn Gln Leu
        35                  40                  45 gtg gtg cca tca gag ggc ctg tac ctc atc tac tcc cag gtc ctc ttc      192
Val Val Pro Ser Glu Gly Leu Tyr Leu Ile Tyr Ser Gln Val Leu Phe
    50                  55                  60 tcg ggc caa ggc tgc ccc tcc acc cat gtg ctc ctc acc cac acc atc      240
Ser Gly Gln Gly Cys Pro Ser Thr His Val Leu Leu Thr His Thr Ile
65                  70                  75                  80 agc cgc atc gcc gtc tcc tac cag acc ccc gtc aac ctc ctc tct gcc      288
Ser Arg Ile Ala Val Ser Tyr Gln Thr Pro Val Asn Leu Leu Ser Ala
                85                  90                  95 atc cgc agc ccc tgc cag agg gag acc cca gag ggg gct gag gcc aac      336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg      384
Pro Trp Tyr Glu Pro Ile Tyr Leu Gly Gly Val Phe Gln Leu Glu Pro
        115                 120                 125 ggt gac cga ctc agc gct gag atc aat cgg ccc gac tat ctc gac ttt      432
Gly Asp Arg Leu Ser Ala Glu Ile Asn Arg Pro Asp Tyr Leu Asp Phe
130                 135                 140 agg gag acg ggg cag gtc tac ttt ggg atc att gcc ctg                  471
Arg Glu Thr Gly Gln Val Tyr Phe Gly Ile Ile Ala Leu
145                 150                 155

<210> SEQ ID NO 31
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 13
<220> FEATURE:
```

```
<221> NAME/KEY: CDS
<222> LOCATION: (1)..(471)

<400> SEQUENCE: 31 gtc aga tca tct tct cga acc ccg agt gac atg cct gta gcc cat gtt      48
Val Arg Ser Ser Ser Arg Thr Pro Ser Asp Met Pro Val Ala His Val
1               5                   10                  15 gta gca aac cct caa gct gag ggg cag ctc cag tgg ctg aac cgc cgg      96
Val Ala Asn Pro Gln Ala Glu Gly Gln Leu Gln Trp Leu Asn Arg Arg
            20                  25                  30 gcc aat gcc ctc ctg gcc aat ggc gtg gag ctg aga gat aac cag ctg     144
Ala Asn Ala Leu Leu Ala Asn Gly Val Glu Leu Arg Asp Asn Gln Leu
        35                  40                  45 gtg gtg cca tca gag ggc ctg tac ctc atc tac tcc cag gtc ctc ttc     192
Val Val Pro Ser Glu Gly Leu Tyr Leu Ile Tyr Ser Gln Val Leu Phe
    50                  55                  60 tcg ggc caa ggc tgc ccc tcc acc cat gtg ctc ctc acc cac acc atc     240
Ser Gly Gln Gly Cys Pro Ser Thr His Val Leu Leu Thr His Thr Ile
65                  70                  75                  80 agc cgc atc gcc gtc tcc tac cag acc ccc gtc aac ctc ctc tct gcc     288
Ser Arg Ile Ala Val Ser Tyr Gln Thr Pro Val Asn Leu Leu Ser Ala
                85                  90                  95 atc cgc agc ccc tgc cag agg gag acc cca gag ggg gct gag gcc aac     336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg     384
Pro Trp Tyr Glu Pro Ile Tyr Leu Gly Gly Val Phe Gln Leu Glu Pro
        115                 120                 125 ggt gac cga ctc agc gct gag atc aat cgg ccc gac tat ctc gac ttt     432
Gly Asp Arg Leu Ser Ala Glu Ile Asn Arg Pro Asp Tyr Leu Asp Phe
    130                 135                 140 gcc gac gac ggg cag gtc tac ttt ggg atc att gcc ctg                 471
Ala Asp Asp Gly Gln Val Tyr Phe Gly Ile Ile Ala Leu
145                 150                 155

<210> SEQ ID NO 32
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 14
<220> FEATURE:
<221> NAME/KEY: CDS
<222> LOCATION: (1)..(471)

<400> SEQUENCE: 32 gtc aga tca tct tct cga acc ccg agt gac atg cct gta gcc cat gtt      48
Val Arg Ser Ser Ser Arg Thr Pro Ser Asp Met Pro Val Ala His Val
1               5                   10                  15 gta gca aac cct caa gct gag ggg cag ctc cag tgg ctg aac cgc cgg      96
Val Ala Asn Pro Gln Ala Glu Gly Gln Leu Gln Trp Leu Asn Arg Arg
            20                  25                  30 gcc aat gcc ctc ctg gcc aat ggc gtg gag ctg aga gat aac cag ctg     144
Ala Asn Ala Leu Leu Ala Asn Gly Val Glu Leu Arg Asp Asn Gln Leu
        35                  40                  45 gtg gtg cca tca gag ggc ctg tac ctc atc tac tcc cag gtc ctc ttc     192
Val Val Pro Ser Glu Gly Leu Tyr Leu Ile Tyr Ser Gln Val Leu Phe
    50                  55                  60 tcg ggc caa ggc tgc ccc tcc acc cat gtg ctc ctc acc cac acc atc     240
Ser Gly Gln Gly Cys Pro Ser Thr His Val Leu Leu Thr His Thr Ile
65                  70                  75                  80
```

```
agc cgc atc gcc gtc tcc tac cag acc ccc gtc aac ctc ctc tct gcc    288
Ser Arg Ile Ala Val Ser Tyr Gln Thr Pro Val Asn Leu Leu Ser Ala
            85                  90                  95 atc cgc agc ccc tgc cag agg gag acc cca gag ggg gct gag gcc aac    336
Ile Arg Ser Pro Cys Gln Arg Glu Thr Pro Glu Gly Ala Glu Ala Asn
        100                 105                 110 ccc tgg tat gag ccc atc tat ctg gga ggg gtc ttc cag ctg gag ccg    384
Pro Trp Tyr Glu Pro Ile Tyr Leu Gly Gly Val Phe Gln Leu Glu Pro
    115                 120                 125 ggt gac cga ctc agc gct gag atc aat cgg ccc gac tat ctc gac ttt    432
Gly Asp Arg Leu Ser Ala Glu Ile Asn Arg Pro Asp Tyr Leu Asp Phe
130                 135                 140 gcc aac gac ggg cag gtc tac ttt ggg atc att gcc ctg                471
Ala Asn Asp Gly Gln Val Tyr Phe Gly Ile Ile Ala Leu
145                 150                 155

<210> SEQ ID NO 33
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 35
<220> FEATURE:
<221> NAME/KEY: CDS
<222> LOCATION: (1)..(471)

<400> SEQUENCE: 33 gtc aga tca tct tct cga acc ccg agt gac atg cct gta gcc cat gtt     48
Val Arg Ser Ser Ser Arg Thr Pro Ser Asp Met Pro Val Ala His Val
1               5                   10                  15 gta gca aac cct caa gct gag ggg cag ctc cag tgg ctg aac cgc cgg     96
Val Ala Asn Pro Gln Ala Glu Gly Gln Leu Gln Trp Leu Asn Arg Arg
            20                  25                  30 gcc aat gcc ctc ctg gcc aat ggc gtg gag ctg aga gat aac cag ctg    144
Ala Asn Ala Leu Leu Ala Asn Gly Val Glu Leu Arg Asp Asn Gln Leu
        35                  40                  45 gtg gtg cca tca gag ggc ctg tac ctc atc tac tcc cag gtc ctc ttc    192
Val Val Pro Ser Glu Gly Leu Tyr Leu Ile Tyr Ser Gln Val Leu Phe
    50                  55                  60 tcg ggc caa ggc tgc ccc tcc acc cat gtg ctc ctc acc cac acc atc    240
Ser Gly Gln Gly Cys Pro Ser Thr His Val Leu Leu Thr His Thr Ile
65                  70                  75                  80 agc cgc atc acc ccc gcc atc aac cgg ccc gtc aac ctc ctc tct gcc    288
Ser Arg Ile Thr Pro Ala Ile Asn Arg Pro Val Asn Leu Leu Ser Ala
            85                  90                  95 atc cgc agc ccc tgc cag agg gag acc cca gag ggg gct gag gcc aac    336
Ile Arg Ser Pro Cys Gln Arg Glu Thr Pro Glu Gly Ala Glu Ala Asn
        100                 105                 110 ccc tgg tat gag ccc atc tat ctg gga ggg gtc ttc cag ctg gag ccg    384
Pro Trp Tyr Glu Pro Ile Tyr Leu Gly Gly Val Phe Gln Leu Glu Pro
    115                 120                 125 ggt gac cga ctc agc gct gag atc aat cgg ccc gac tat ctc gac ttt    432
Gly Asp Arg Leu Ser Ala Glu Ile Asn Arg Pro Asp Tyr Leu Asp Phe
130                 135                 140 gcc gag tct ggg cag gtc tac ttt ggg atc att gcc ctg                471
Ala Glu Ser Gly Gln Val Tyr Phe Gly Ile Ile Ala Leu
145                 150                 155

<210> SEQ ID NO 34
<211> LENGTH: 471
```

<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 36
<220> FEATURE:
<221> NAME/KEY: CDS
<222> LOCATION: (1)..(471)

<400> SEQUENCE: 34

```
gtc aga tca tct tct cga acc ccg agt gac atg cct gta gcc cat gtt      48
Val Arg Ser Ser Ser Arg Thr Pro Ser Asp Met Pro Val Ala His Val
1               5                   10                  15 gta gca aac cct caa gct gag ggg cag ctc cag tgg ctg aac cgc cgg      96
Val Ala Asn Pro Gln Ala Glu Gly Gln Leu Gln Trp Leu Asn Arg Arg
            20                  25                  30 gcc aat gcc ctc ctg gcc aat ggc gtg gag ctg aga gat aac cag ctg     144
Ala Asn Ala Leu Leu Ala Asn Gly Val Glu Leu Arg Asp Asn Gln Leu
        35                  40                  45 gtg gtg cca tca gag ggc ctg tac ctc atc tac tcc cag gtc ctc ttc     192
Val Val Pro Ser Glu Gly Leu Tyr Leu Ile Tyr Ser Gln Val Leu Phe
    50                  55                  60 tcg ggc caa ggc tgc ccc tcc acc cat gtg ctc ctc acc cac acc atc     240
Ser Gly Gln Gly Cys Pro Ser Thr His Val Leu Leu Thr His Thr Ile
65                  70                  75                  80 agc cgc atc gcg ccc ggc tac tcc cac ccc gtc aac ctc ctc tct gcc     288
Ser Arg Ile Ala Pro Gly Tyr Ser His Pro Val Asn Leu Leu Ser Ala
                85                  90                  95 atc cgc agc ccc tgc cag agg gag acc cca gag ggg gct gag gcc aac     336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg     384
Pro Trp Tyr Glu Pro Ile Tyr Leu Gly Gly Val Phe Gln Leu Glu Pro
        115                 120                 125 ggt gac cga ctc agc gct gag atc aat cgg ccc gac tat ctc gac ttt     432
Gly Asp Arg Leu Ser Ala Glu Ile Asn Arg Pro Asp Tyr Leu Asp Phe
    130                 135                 140 gcc gag tct ggg cag gtc tac ttt ggg atc att gcc ctg                 471
Ala Glu Ser Gly Gln Val Tyr Phe Gly Ile Ile Ala Leu
145                 150                 155
```

<210> SEQ ID NO 35
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 37
<220> FEATURE:
<221> NAME/KEY: CDS
<222> LOCATION: (1)..(471)

<400> SEQUENCE: 35

```
gtc aga tca tct tct cga acc ccg agt gac atg cct gta gcc cat gtt      48
Val Arg Ser Ser Ser Arg Thr Pro Ser Asp Met Pro Val Ala His Val
1               5                   10                  15 gta gca aac cct caa gct gag ggg cag ctc cag tgg ctg aac cgc cgg      96
Val Ala Asn Pro Gln Ala Glu Gly Gln Leu Gln Trp Leu Asn Arg Arg
            20                  25                  30 gcc aat gcc ctc ctg gcc aat ggc gtg gag ctg aga gat aac cag ctg     144
Ala Asn Ala Leu Leu Ala Asn Gly Val Glu Leu Arg Asp Asn Gln Leu
        35                  40                  45
```

```
gtg gtg cca tca gag ggc ctg tac ctc atc tac tcc cag gtc ctc ttc      192
Val Val Pro Ser Glu Gly Leu Tyr Leu Ile Tyr Ser Gln Val Leu Phe
 50                  55                  60 tcg ggc caa ggc tgc ccc tcc acc cat gtg ctc ctc acc cac acc atc      240
Ser Gly Gln Gly Cys Pro Ser Thr His Val Leu Leu Thr His Thr Ile
 65                  70                  75                  80 agc cgc atc agc acc acc cac aac cag ccc gtc aac ctc ctc tct gcc      288
Ser Arg Ile Ser Thr Thr His Asn Gln Pro Val Asn Leu Leu Ser Ala
                 85                  90                  95 atc cgc agc ccc tgc cag agg gag acc cca gag ggg gct gag gcc aac      336
Ile Arg Ser Pro Cys Gln Arg Glu Thr Pro Glu Gly Ala Glu Ala Asn
                100                 105                 110 ccc tgg tat gag ccc atc tat ctg gga ggg gtc ttc cag ctg gag ccg      384
Pro Trp Tyr Glu Pro Ile Tyr Leu Gly Gly Val Phe Gln Leu Glu Pro
                115                 120                 125 ggt gac cga ctc agc gct gag atc aat cgg ccc gac tat ctc gac ttt      432
Gly Asp Arg Leu Ser Ala Glu Ile Asn Arg Pro Asp Tyr Leu Asp Phe
130                 135                 140 gcc gag tct ggg cag gtc tac ttt ggg atc att gcc ctg                  471
Ala Glu Ser Gly Gln Val Tyr Phe Gly Ile Ile Ala Leu
145                 150                 155

<210> SEQ ID NO 36
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 38
<220> FEATURE:
<221> NAME/KEY: CDS
<222> LOCATION: (1)..(471)

<400> SEQUENCE: 36 gtc aga tca tct tct cga acc ccg agt gac atg cct gta gcc cat gtt       48
Val Arg Ser Ser Ser Arg Thr Pro Ser Asp Met Pro Val Ala His Val
  1               5                  10                  15 gta gca aac cct caa gct gag ggg cag ctc cag tgg ctg aac cgc cgg       96
Val Ala Asn Pro Gln Ala Glu Gly Gln Leu Gln Trp Leu Asn Arg Arg
                 20                  25                  30 gcc aat gcc ctc ctg gcc aat ggc gtg gag ctg aga gat aac cag ctg      144
Ala Asn Ala Leu Leu Ala Asn Gly Val Glu Leu Arg Asp Asn Gln Leu
             35                  40                  45 gtg gtg cca tca gag ggc ctg tac ctc atc tac tcc cag gtc ctc ttc      192
Val Val Pro Ser Glu Gly Leu Tyr Leu Ile Tyr Ser Gln Val Leu Phe
 50                  55                  60 tcg ggc caa ggc tgc ccc tcc acc cat gtg ctc ctc acc cac acc atc      240
Ser Gly Gln Gly Cys Pro Ser Thr His Val Leu Leu Thr His Thr Ile
 65                  70                  75                  80 agc cgc atc ggc ggc ccg tac cag cgg ccc gtc aac ctc ctc tct gcc      288
Ser Arg Ile Gly Gly Pro Tyr Gln Arg Pro Val Asn Leu Leu Ser Ala
                 85                  90                  95 atc cgc agc ccc tgc cag agg gag acc cca gag ggg gct gag gcc aac      336
Ile Arg Ser Pro Cys Gln Arg Glu Thr Pro Glu Gly Ala Glu Ala Asn
                100                 105                 110 ccc tgg tat gag ccc atc tat ctg gga ggg gtc ttc cag ctg gag ccg      384
Pro Trp Tyr Glu Pro Ile Tyr Leu Gly Gly Val Phe Gln Leu Glu Pro
                115                 120                 125 ggt gac cga ctc agc gct gag atc aat cgg ccc gac tat ctc gac ttt      432
Gly Asp Arg Leu Ser Ala Glu Ile Asn Arg Pro Asp Tyr Leu Asp Phe
130                 135                 140
```

```
                                -continued gcc gag tct ggg cag gtc tac ttt ggg atc att gcc ctg            471
Ala Glu Ser Gly Gln Val Tyr Phe Gly Ile Ile Ala Leu
145                 150                 155

<210> SEQ ID NO 37
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 1

<400> SEQUENCE: 37

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Gln Asn Arg Trp
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
65                  70                  75                  80

Ser Arg Ile Ala Val Ser Tyr Gln Thr Pro Val Asn Leu Leu Ser Ala
                85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 38
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 2

<400> SEQUENCE: 38

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Thr Asn Gly Tyr
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
65                  70                  75                  80

Ser Arg Ile Ala Val Ser Tyr Gln Thr Pro Val Asn Leu Leu Ser Ala
                85                  90                  95

Ile Arg Ser Pro Cys Gln Arg Glu Thr Pro Glu Gly Ala Glu Ala Asn
```

```
                100             105                 110
Pro Trp Tyr Glu Pro Ile Tyr Leu Gly Gly Val Phe Gln Leu Glu Pro
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 39
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 3

<400> SEQUENCE: 39

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Ser Asp
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
65                  70                  75                  80

Ser Arg Ile Ala Val Ser Tyr Gln Thr Pro Val Asn Leu Leu Ser Ala
                85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
        115                 120                 125

Gly Asp Arg Leu Ser Ala Glu Ile Asn Arg Pro Asp Tyr Leu Asp Phe
    130                 135                 140

Ala Ala Arg Gly Gln Val Tyr Phe Gly Ile Ile Ala Leu
145                 150                 155

<210> SEQ ID NO 40
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 4

<400> SEQUENCE: 40

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Lys Asn Ala Gly
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
```

```
                65                  70                  75                  80
Ser Arg Ile Ala Val Ser Tyr Gln Thr Pro Val Asn Leu Leu Ser Ala
                    85                  90                  95

Ile Arg Ser Pro Cys Gln Arg Glu Thr Pro Glu Gly Ala Glu Ala Asn
                    100                 105                 110

Pro Trp Tyr Glu Pro Ile Tyr Leu Gly Gly Val Phe Gln Leu Glu Pro
                    115                 120                 125

Gly Asp Arg Leu Ser Ala Glu Ile Asn Arg Pro Asp Tyr Leu Asp Phe
            130                 135                 140

Ala Ser Thr Gly Gln Val Tyr Phe Gly Ile Ile Ala Leu
145                 150                 155

<210> SEQ ID NO 41
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 16

<400> SEQUENCE: 41

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
        50                  55                  60

Ser Gly Gln Gly Cys Pro Ser Thr His Val Leu Leu Thr His Thr Ile
65                  70                  75                  80

Ser Arg Ile Ser Ser Thr Tyr Pro Asp Pro Val Asn Leu Leu Ser Ala
                    85                  90                  95

Ile Arg Ser Pro Cys Gln Arg Glu Thr Pro Glu Gly Ala Glu Ala Asn
                    100                 105                 110

Pro Trp Tyr Glu Pro Ile Tyr Leu Gly Gly Val Phe Gln Leu Glu Pro
                    115                 120                 125

Gly Asp Arg Leu Ser Ala Glu Ile Asn Arg Pro Asp Tyr Leu Asp Phe
            130                 135                 140

Ala Glu Ser Gly Gln Val Tyr Phe Gly Ile Ile Ala Leu
145                 150                 155

<210> SEQ ID NO 42
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 17

<400> SEQUENCE: 42

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
```

```
                35                  40                  45
Val Val Pro Ser Glu Gly Leu Tyr Leu Ile Tyr Ser Gln Val Leu Phe
 50                  55                  60

Ser Gly Gln Gly Cys Pro Ser Thr His Val Leu Leu Thr His Thr Ile
 65                  70                  75                  80

Ser Arg Ile Ser Lys Thr Tyr Thr His Pro Val Asn Leu Leu Ser Ala
                 85                  90                  95

Ile Arg Ser Pro Cys Gln Arg Glu Thr Pro Glu Gly Ala Glu Ala Asn
                100                 105                 110

Pro Trp Tyr Glu Pro Ile Tyr Leu Gly Gly Val Phe Gln Leu Glu Pro
                115                 120                 125

Gly Asp Arg Leu Ser Ala Glu Ile Asn Arg Pro Asp Tyr Leu Asp Phe
                130                 135                 140

Ala Glu Ser Gly Gln Val Tyr Phe Gly Ile Ile Ala Leu
145                 150                 155
```

<210> SEQ ID NO 43
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 18

<400> SEQUENCE: 43

```
Val Arg Ser Ser Ser Arg Thr Pro Ser Asp Met Pro Val Ala His Val
 1               5                  10                  15

Val Ala Asn Pro Gln Ala Glu Gly Gln Leu Gln Trp Leu Asn Arg Arg
                 20                  25                  30

Ala Asn Ala Leu Leu Ala Asn Gly Val Glu Leu Arg Asp Asn Gln Leu
                 35                  40                  45

Val Val Pro Ser Glu Gly Leu Tyr Leu Ile Tyr Ser Gln Val Leu Phe
 50                  55                  60

Ser Gly Gln Gly Cys Pro Ser Thr His Val Leu Leu Thr His Thr Ile
 65                  70                  75                  80

Ser Arg Ile Ser Pro Leu Tyr Pro Lys Pro Val Asn Leu Leu Ser Ala
                 85                  90                  95

Ile Arg Ser Pro Cys Gln Arg Glu Thr Pro Glu Gly Ala Glu Ala Asn
                100                 105                 110

Pro Trp Tyr Glu Pro Ile Tyr Leu Gly Gly Val Phe Gln Leu Glu Pro
                115                 120                 125

Gly Asp Arg Leu Ser Ala Glu Ile Asn Arg Pro Asp Tyr Leu Asp Phe
                130                 135                 140

Ala Glu Ser Gly Gln Val Tyr Phe Gly Ile Ile Ala Leu
145                 150                 155
```

<210> SEQ ID NO 44
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 19

<400> SEQUENCE: 44

Val Arg Ser Ser Ser Arg Thr Pro Ser Asp Met Pro Val Ala His Val

```
                1               5              10              15
Val Ala Asn Pro Gln Ala Glu Gly Gln Leu Gln Trp Leu Asn Arg Arg
                20                  25                  30
Ala Asn Ala Leu Leu Ala Asn Gly Val Glu Leu Arg Asp Asn Gln Leu
                35                  40                  45
Val Val Pro Ser Glu Gly Leu Tyr Leu Ile Tyr Ser Gln Val Leu Phe
            50                  55                  60
Ser Gly Gln Gly Cys Pro Ser Thr His Val Leu Thr His Thr Ile
 65                 70                  75                  80
Ser Arg Ile Ser Tyr Asn Tyr Asn Gly Pro Val Asn Leu Leu Ser Ala
                    85                  90                  95
Ile Arg Ser Pro Cys Gln Arg Glu Thr Pro Glu Gly Ala Glu Ala Asn
                100                 105                 110
Pro Trp Tyr Glu Pro Ile Tyr Leu Gly Gly Val Phe Gln Leu Glu Pro
                115                 120                 125
Gly Asp Arg Leu Ser Ala Glu Ile Asn Arg Pro Asp Tyr Leu Asp Phe
                130                 135                 140
Ala Glu Ser Gly Gln Val Tyr Phe Gly Ile Ile Ala Leu
145                 150                 155

<210> SEQ ID NO 45
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 20

<400> SEQUENCE: 45

Val Arg Ser Ser Ser Arg Thr Pro Ser Asp Met Pro Val Ala His Val
 1               5                  10                  15
Val Ala Asn Pro Gln Ala Glu Gly Gln Leu Gln Trp Leu Asn Arg Arg
                20                  25                  30
Ala Asn Ala Leu Leu Ala Asn Gly Val Glu Leu Arg Asp Asn Gln Leu
                35                  40                  45
Val Val Pro Ser Glu Gly Leu Tyr Leu Ile Tyr Ser Gln Val Leu Phe
            50                  55                  60
Ser Gly Gln Gly Cys Pro Ser Thr His Val Leu Leu Thr His Thr Ile
 65                 70                  75                  80
Ser Arg Ile Ser Ser Ala Tyr Ala Ser Pro Val Asn Leu Leu Ser Ala
                    85                  90                  95
Ile Arg Ser Pro Cys Gln Arg Glu Thr Pro Glu Gly Ala Glu Ala Asn
                100                 105                 110
Pro Trp Tyr Glu Pro Ile Tyr Leu Gly Gly Val Phe Gln Leu Glu Pro
                115                 120                 125
Gly Asp Arg Leu Ser Ala Glu Ile Asn Arg Pro Asp Tyr Leu Asp Phe
                130                 135                 140
Ala Glu Ser Gly Gln Val Tyr Phe Gly Ile Ile Ala Leu
145                 150                 155

<210> SEQ ID NO 46
<211> LENGTH: 157
<212> TYPE: PRT
<213> ORGANISM: Artificial Sequence
<220> FEATURE:
<223> OTHER INFORMATION: Synthetic
<220> FEATURE:
```

```
<221> NAME/KEY: misc_feature
<223> OTHER INFORMATION: Clone No. 21

<400> SEQUENCE: 46

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
65                  70                  75                  80

Ser Arg Ile Thr Ser Ala Tyr Gly Pro Pro Val Asn Leu Leu Ser Ala
                85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 47
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 22

<400> SEQUENCE: 47

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
65                  70                  75                  80

Ser Arg Ile Ser Arg Val Tyr Thr Ala Pro Val Asn Leu Leu Ser Ala
                85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 48
```

```
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 23

<400> SEQUENCE: 48

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
65                  70                  75                  80

Ser Arg Ile Thr Thr Ala Tyr Ser Gly Pro Val Asn Leu Leu Ser Ala
                85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 49
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 24

<400> SEQUENCE: 49

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
65                  70                  75                  80

Ser Arg Ile Thr His Lys Tyr Pro Gln Pro Val Asn Leu Leu Ser Ala
                85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
        115                 120                 125

Gly Asp Arg Leu Ser Ala Glu Ile Asn Arg Pro Asp Tyr Leu Asp Phe
    130                 135                 140
```

```
Ala Glu Ser Gly Gln Val Tyr Phe Gly Ile Ile Ala Leu
145                 150                 155

<210> SEQ ID NO 50
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 25

<400> SEQUENCE: 50

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
65                  70                  75                  80

Ser Arg Ile Ser Lys Thr Tyr Ser His Pro Val Asn Leu Leu Ser Ala
                85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 51
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 26

<400> SEQUENCE: 51

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
65                  70                  75                  80

Ser Arg Ile Ser Ser His Tyr Arg Phe Pro Val Asn Leu Leu Ser Ala
                85                  90                  95

Ile Arg Ser Pro Cys Gln Arg Glu Thr Pro Glu Gly Ala Glu Ala Asn
            100                 105                 110
```

Pro Trp Tyr Glu Pro Ile Tyr Leu Gly Gly Val Phe Gln Leu Glu Pro
        115                 120                 125

Gly Asp Arg Leu Ser Ala Glu Ile Asn Arg Pro Asp Tyr Leu Asp Phe
        130                 135                 140

Ala Glu Ser Gly Gln Val Tyr Phe Gly Ile Ile Ala Leu
145                 150                 155

<210> SEQ ID NO 52
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 27

<400> SEQUENCE: 52

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
65                  70                  75                  80

Ser Arg Ile Thr Pro Ala Tyr Pro Arg Pro Val Asn Leu Leu Ser Ala
                85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
        115                 120                 125

Gly Asp Arg Leu Ser Ala Glu Ile Asn Arg Pro Asp Tyr Leu Asp Phe
        130                 135                 140

Ala Glu Ser Gly Gln Val Tyr Phe Gly Ile Ile Ala Leu
145                 150                 155

<210> SEQ ID NO 53
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 28

<400> SEQUENCE: 53

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
65                  70                  75                  80

```
Ser Arg Ile Thr Lys Ser Tyr Ser Lys Pro Val Asn Leu Leu Ser Ala
                85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 54
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 29

<400> SEQUENCE: 54

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
65                  70                  75                  80

Ser Arg Ile Thr Glu Gln Tyr Ser His Pro Val Asn Leu Leu Ser Ala
                85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 55
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 30

<400> SEQUENCE: 55

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45
```

Val Val Pro Ser Glu Gly Leu Tyr Leu Ile Tyr Ser Gln Val Leu Phe
            50                  55                  60

Ser Gly Gln Gly Cys Pro Ser Thr His Val Leu Leu Thr His Thr Ile
 65                  70                  75                  80

Ser Arg Ile Thr Pro Gly Tyr Pro Ser Pro Val Asn Leu Leu Ser Ala
                85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
            115                 120                 125

Gly Asp Arg Leu Ser Ala Glu Ile Asn Arg Pro Asp Tyr Leu Asp Phe
            130                 135                 140

Ala Glu Ser Gly Gln Val Tyr Phe Gly Ile Ile Ala Leu
145                 150                 155

<210> SEQ ID NO 56
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 31

<400> SEQUENCE: 56

Val Arg Ser Ser Ser Arg Thr Pro Ser Asp Met Pro Val Ala His Val
 1               5                  10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
            50                  55                  60

Ser Gly Gln Gly Cys Pro Ser Thr His Val Leu Leu Thr His Thr Ile
 65                  70                  75                  80

Ser Arg Ile Ser Lys Thr Tyr Ser His Pro Val Asn Leu Leu Ser Ala
                85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
            115                 120                 125

Gly Asp Arg Leu Ser Ala Glu Ile Asn Arg Pro Asp Tyr Leu Asp Phe
            130                 135                 140

Ala Glu Ser Gly Gln Val Tyr Phe Gly Ile Ile Ala Leu
145                 150                 155

<210> SEQ ID NO 57
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 32

<400> SEQUENCE: 57

Val Arg Ser Ser Ser Arg Thr Pro Ser Asp Met Pro Val Ala His Val
 1               5                  10                  15

```
Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
65                  70                  75                  80

Ser Arg Ile Thr Asp Arg Tyr Ser Ser Pro Val Asn Leu Leu Ser Ala
                85                  90                  95

Ile Arg Ser Pro Cys Gln Arg Glu Thr Pro Glu Gly Ala Glu Ala Asn
                100                 105                 110

Pro Trp Tyr Glu Pro Ile Tyr Leu Gly Gly Val Phe Gln Leu Glu Pro
            115                 120                 125

Gly Asp Arg Leu Ser Ala Glu Ile Asn Arg Pro Asp Tyr Leu Asp Phe
130                 135                 140

Ala Glu Ser Gly Gln Val Tyr Phe Gly Ile Ile Ala Leu
145                 150                 155

<210> SEQ ID NO 58
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 33

<400> SEQUENCE: 58

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
65                  70                  75                  80

Ser Arg Ile Asn His Arg Tyr Gln Asp Pro Val Asn Leu Leu Ser Ala
                85                  90                  95

Ile Arg Ser Pro Cys Gln Arg Glu Thr Pro Glu Gly Ala Glu Ala Asn
                100                 105                 110

Pro Trp Tyr Glu Pro Ile Tyr Leu Gly Gly Val Phe Gln Leu Glu Pro
            115                 120                 125

Gly Asp Arg Leu Ser Ala Glu Ile Asn Arg Pro Asp Tyr Leu Asp Phe
130                 135                 140

Ala Glu Ser Gly Gln Val Tyr Phe Gly Ile Ile Ala Leu
145                 150                 155

<210> SEQ ID NO 59
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: misc_feature
```

<223> OTHER INFORMATION: Clone No. 34

<400> SEQUENCE: 59

```
Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
65                  70                  75                  80

Ser Arg Ile Ser Ala Asp Tyr Pro His Pro Val Asn Leu Leu Ser Ala
                85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155
```

<210> SEQ ID NO 60
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 1
<220> FEATURE:
<221> NAME/KEY: CDS
<222> LOCATION: (1)..(471)

<400> SEQUENCE: 60

```
gtc aga tca tct tct cga acc ccg agt gac atg cct gta gcc cat gtt      48
Val Arg Ser Ser Ser Arg Thr Pro Ser Asp Met Pro Val Ala His Val
1               5                   10                  15 gta gca aac cct caa gct gag ggg cag ctc cag tgg cag aac agg tgg      96
Val Ala Asn Pro Gln Ala Glu Gly Gln Leu Gln Trp Gln Asn Arg Trp
            20                  25                  30 gcc aat gcc ctc ctg gcc aat ggc gtg gag ctg aga gat aac cag ctg     144
Ala Asn Ala Leu Leu Ala Asn Gly Val Glu Leu Arg Asp Asn Gln Leu
        35                  40                  45 gtg gtg cca tca gag ggc ctg tac ctc atc tac tcc cag gtc ctc ttc     192
Val Val Pro Ser Glu Gly Leu Tyr Leu Ile Tyr Ser Gln Val Leu Phe
    50                  55                  60 tcg ggc caa ggc tgc ccc tcc acc cat gtg ctc ctc acc cac acc atc     240
Ser Gly Gln Gly Cys Pro Ser Thr His Val Leu Leu Thr His Thr Ile
65                  70                  75                  80 agc cgc atc gcc gtc tcc tac cag acc ccc gtc aac ctc ctc tct gcc     288
Ser Arg Ile Ala Val Ser Tyr Gln Thr Pro Val Asn Leu Leu Ser Ala
                85                  90                  95 atc cgc agc ccc tgc cag agg gag acc cca gag ggg gct gag gcc aac     336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg     384
Pro Trp Tyr Glu Pro Ile Tyr Leu Gly Gly Val Phe Gln Leu Glu Pro
```

```
                115                 120                 125
ggt gac cga ctc agc gct gag atc aat cgg ccc gac tat ctc gac ttt        432
Gly Asp Arg Leu Ser Ala Glu Ile Asn Arg Pro Asp Tyr Leu Asp Phe
        130                 135                 140 gcc gag tct ggg cag gtc tac ttt ggg atc att gcc ctg                    471
Ala Glu Ser Gly Gln Val Tyr Phe Gly Ile Ile Ala Leu
145                 150                 155

<210> SEQ ID NO 61
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 2
<220> FEATURE:
<221> NAME/KEY: CDS
<222> LOCATION: (1)..(471)

<400> SEQUENCE: 61 gtc aga tca tct tct cga acc ccg agt gac atg cct gta gcc cat gtt         48
Val Arg Ser Ser Ser Arg Thr Pro Ser Asp Met Pro Val Ala His Val
1               5                   10                  15 gta gca aac cct caa gct gag ggg cag ctc cag tgg acg aac ggg tac         96
Val Ala Asn Pro Gln Ala Glu Gly Gln Leu Gln Trp Thr Asn Gly Tyr
            20                  25                  30 gcc aat gcc ctc ctg gcc aat ggc gtg gag ctg aga gat aac cag ctg        144
Ala Asn Ala Leu Leu Ala Asn Gly Val Glu Leu Arg Asp Asn Gln Leu
        35                  40                  45 gtg gtg cca tca gag ggc ctg tac ctc atc tac tcc cag gtc ctc ttc        192
Val Val Pro Ser Glu Gly Leu Tyr Leu Ile Tyr Ser Gln Val Leu Phe
    50                  55                  60 tcg ggc caa ggc tgc ccc tcc acc cat gtg ctc ctc acc cac acc atc        240
Ser Gly Gln Gly Cys Pro Ser Thr His Val Leu Leu Thr His Thr Ile
65                  70                  75                  80 agc cgc atc gcc gtc tcc tac cag acc ccc gtc aac ctc ctc tct gcc        288
Ser Arg Ile Ala Val Ser Tyr Gln Thr Pro Val Asn Leu Leu Ser Ala
                85                  90                  95 atc cgc agc ccc tgc cag agg gag acc cca gag ggg gct gag gcc aac        336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg        384
Pro Trp Tyr Glu Pro Ile Tyr Leu Gly Gly Val Phe Gln Leu Glu Pro
        115                 120                 125 ggt gac cga ctc agc gct gag atc aat cgg ccc gac tat ctc gac ttt        432
Gly Asp Arg Leu Ser Ala Glu Ile Asn Arg Pro Asp Tyr Leu Asp Phe
    130                 135                 140 gcc gag tct ggg cag gtc tac ttt ggg atc att gcc ctg                    471
Ala Glu Ser Gly Gln Val Tyr Phe Gly Ile Ile Ala Leu
145                 150                 155

<210> SEQ ID NO 62
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 3
<220> FEATURE:
<221> NAME/KEY: CDS
<222> LOCATION: (1)..(471)
```

-continued

```
<400> SEQUENCE: 62 gtc aga tca tct tct cga acc ccg agt gac atg cct gta gcc cat gtt     48
Val Arg Ser Ser Ser Arg Thr Pro Ser Asp Met Pro Val Ala His Val
1               5                   10                  15 gta gca aac cct caa gct gag ggg cag ctc cag tgg tcc aac agc gac     96
Val Ala Asn Pro Gln Ala Glu Gly Gln Leu Gln Trp Ser Asn Ser Asp
            20                  25                  30 gcc aat gcc ctc ctg gcc aat ggc gtg gag ctg aga gat aac cag ctg    144
Ala Asn Ala Leu Leu Ala Asn Gly Val Glu Leu Arg Asp Asn Gln Leu
        35                  40                  45 gtg gtg cca tca gag ggc ctg tac ctc atc tac tcc cag gtc ctc ttc    192
Val Val Pro Ser Glu Gly Leu Tyr Leu Ile Tyr Ser Gln Val Leu Phe
    50                  55                  60 tcg ggc caa ggc tgc ccc tcc acc cat gtg ctc ctc acc cac acc atc    240
Ser Gly Gln Gly Cys Pro Ser Thr His Val Leu Leu Thr His Thr Ile
65                  70                  75                  80 agc cgc atc gcc gtc tcc tac cag acc ccc gtc aac ctc ctc tct gcc    288
Ser Arg Ile Ala Val Ser Tyr Gln Thr Pro Val Asn Leu Leu Ser Ala
                85                  90                  95 atc cgc agc ccc tgc cag agg gag acc cca gag ggg gct gag gcc aac    336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg    384
Pro Trp Tyr Glu Pro Ile Tyr Leu Gly Gly Val Phe Gln Leu Glu Pro
        115                 120                 125 ggt gac cga ctc agc gct gag atc aat cgg ccc gac tat ctc gac ttt    432
Gly Asp Arg Leu Ser Ala Glu Ile Asn Arg Pro Asp Tyr Leu Asp Phe
    130                 135                 140 gcc gcc cgc ggg cag gtc tac ttt ggg atc att gcc ctg                471
Ala Ala Arg Gly Gln Val Tyr Phe Gly Ile Ile Ala Leu
145                 150                 155

<210> SEQ ID NO 63
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 4
<220> FEATURE:
<221> NAME/KEY: CDS
<222> LOCATION: (1)..(471)

<400> SEQUENCE: 63 gtc aga tca tct tct cga acc ccg agt gac atg cct gta gcc cat gtt     48
Val Arg Ser Ser Ser Arg Thr Pro Ser Asp Met Pro Val Ala His Val
1               5                   10                  15 gta gca aac cct caa gct gag ggg cag ctc cag tgg aag aac gcc ggc     96
Val Ala Asn Pro Gln Ala Glu Gly Gln Leu Gln Trp Lys Asn Ala Gly
            20                  25                  30 gcc aat gcc ctc ctg gcc aat ggc gtg gag ctg aga gat aac cag ctg    144
Ala Asn Ala Leu Leu Ala Asn Gly Val Glu Leu Arg Asp Asn Gln Leu
        35                  40                  45 gtg gtg cca tca gag ggc ctg tac ctc atc tac tcc cag gtc ctc ttc    192
Val Val Pro Ser Glu Gly Leu Tyr Leu Ile Tyr Ser Gln Val Leu Phe
    50                  55                  60 tcg ggc caa ggc tgc ccc tcc acc cat gtg ctc ctc acc cac acc atc    240
Ser Gly Gln Gly Cys Pro Ser Thr His Val Leu Leu Thr His Thr Ile
65                  70                  75                  80 agc cgc atc gcc gtc tcc tac cag acc ccc gtc aac ctc ctc tct gcc    288
Ser Arg Ile Ala Val Ser Tyr Gln Thr Pro Val Asn Leu Leu Ser Ala
```

```
atc cgc agc ccc tgc cag agg gag acc cca gag ggg gct gag gcc aac       336
Ile Arg Ser Pro Cys Gln Arg Glu Thr Pro Glu Gly Ala Glu Ala Asn
        100                 105                 110 ccc tgg tat gag ccc atc tat ctg gga ggg gtc ttc cag ctg gag ccg       384
Pro Trp Tyr Glu Pro Ile Tyr Leu Gly Gly Val Phe Gln Leu Glu Pro
            115                 120                 125 ggt gac cga ctc agc gct gag atc aat cgg ccc gac tat ctc gac ttt       432
Gly Asp Arg Leu Ser Ala Glu Ile Asn Arg Pro Asp Tyr Leu Asp Phe
    130                 135                 140 gct tcg acg ggg cag gtc tac ttt ggg atc att gcc ctg                   471
Ala Ser Thr Gly Gln Val Tyr Phe Gly Ile Ile Ala Leu
145                 150                 155
```

<210> SEQ ID NO 64
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 16
<220> FEATURE:
<221> NAME/KEY: CDS
<222> LOCATION: (1)..(471)

<400> SEQUENCE: 64

```
gtc aga tca tct tct cga acc ccg agt gac atg cct gta gcc cat gtt        48
Val Arg Ser Ser Ser Arg Thr Pro Ser Asp Met Pro Val Ala His Val
1               5                   10                  15 gta gca aac cct caa gct gag ggg cag ctc cag tgg ctg aac cgc cgg        96
Val Ala Asn Pro Gln Ala Glu Gly Gln Leu Gln Trp Leu Asn Arg Arg
            20                  25                  30 gcc aat gcc ctc ctg gcc aat ggc gtg gag ctg aga gat aac cag ctg       144
Ala Asn Ala Leu Leu Ala Asn Gly Val Glu Leu Arg Asp Asn Gln Leu
        35                  40                  45 gtg gtg cca tca gag ggc ctg tac ctc atc tac tcc cag gtc ctc ttc       192
Val Val Pro Ser Glu Gly Leu Tyr Leu Ile Tyr Ser Gln Val Leu Phe
    50                  55                  60 tcg ggc caa ggc tgc ccc tcc acc cat gtg ctc ctc acc cac acc atc       240
Ser Gly Gln Gly Cys Pro Ser Thr His Val Leu Leu Thr His Thr Ile
65                  70                  75                  80 agc cgc atc agc tcg acc tac ccc gac ccc gtc aac ctc ctc tct gcc       288
Ser Arg Ile Ser Ser Thr Tyr Pro Asp Pro Val Asn Leu Leu Ser Ala
                85                  90                  95 atc cgc agc ccc tgc cag agg gag acc cca gag ggg gct gag gcc aac       336
Ile Arg Ser Pro Cys Gln Arg Glu Thr Pro Glu Gly Ala Glu Ala Asn
        100                 105                 110 ccc tgg tat gag ccc atc tat ctg gga ggg gtc ttc cag ctg gag ccg       384
Pro Trp Tyr Glu Pro Ile Tyr Leu Gly Gly Val Phe Gln Leu Glu Pro
            115                 120                 125 ggt gac cga ctc agc gct gag atc aat cgg ccc gac tat ctc gac ttt       432
Gly Asp Arg Leu Ser Ala Glu Ile Asn Arg Pro Asp Tyr Leu Asp Phe
    130                 135                 140 gcc gag tct ggg cag gtc tac ttt ggg atc att gcc ctg                   471
Ala Glu Ser Gly Gln Val Tyr Phe Gly Ile Ile Ala Leu
145                 150                 155
```

<210> SEQ ID NO 65
<211> LENGTH: 471
<212> TYPE: DNA
<213> ORGANISM: Artificial Sequence
<220> FEATURE:

-continued

```
<223> OTHER INFORMATION: Synthetic
<220> FEATURE:
<221> NAME/KEY: misc_feature
<223> OTHER INFORMATION: Clone No. 17
<220> FEATURE:
<221> NAME/KEY: CDS
<222> LOCATION: (1)..(471)

<400> SEQUENCE: 65 gtc aga tca tct tct cga acc ccg agt gac atg cct gta gcc cat gtt      48
Val Arg Ser Ser Ser Arg Thr Pro Ser Asp Met Pro Val Ala His Val
1               5                  10                 15 gta gca aac cct caa gct gag ggg cag ctc cag tgg ctg aac cgc cgg      96
Val Ala Asn Pro Gln Ala Glu Gly Gln Leu Gln Trp Leu Asn Arg Arg
            20                  25                  30 gcc aat gcc ctc ctg gcc aat ggc gtg gag ctg aga gat aac cag ctg     144
Ala Asn Ala Leu Leu Ala Asn Gly Val Glu Leu Arg Asp Asn Gln Leu
        35                  40                  45 gtg gtg cca tca gag ggc ctg tac ctc atc tac tcc cag gtc ctc ttc     192
Val Val Pro Ser Glu Gly Leu Tyr Leu Ile Tyr Ser Gln Val Leu Phe
    50                  55                  60 tcg ggc caa ggc tgc ccc tcc acc cat gtg ctc ctc acc cac acc atc     240
Ser Gly Gln Gly Cys Pro Ser Thr His Val Leu Leu Thr His Thr Ile
65                  70                  75                  80 agc cgc atc tcg aag acc tac acc cac ccc gtc aac ctc ctc tct gcc     288
Ser Arg Ile Ser Lys Thr Tyr Thr His Pro Val Asn Leu Leu Ser Ala
                85                  90                  95 atc cgc agc ccc tgc cag agg gag acc cca gag ggg gct gag gcc aac     336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg     384
Pro Trp Tyr Glu Pro Ile Tyr Leu Gly Gly Val Phe Gln Leu Glu Pro
        115                 120                 125 ggt gac cga ctc agc gct gag atc aat cgg ccc gac tat ctc gac ttt     432
Gly Asp Arg Leu Ser Ala Glu Ile Asn Arg Pro Asp Tyr Leu Asp Phe
    130                 135                 140 gcc gag tct ggg cag gtc tac ttt ggg atc att gcc ctg                 471
Ala Glu Ser Gly Gln Val Tyr Phe Gly Ile Ile Ala Leu
145                 150                 155

<210> SEQ ID NO 66
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 18
<220> FEATURE:
<221> NAME/KEY: CDS
<222> LOCATION: (1)..(471)

<400> SEQUENCE: 66 gtc aga tca tct tct cga acc ccg agt gac atg cct gta gcc cat gtt      48
Val Arg Ser Ser Ser Arg Thr Pro Ser Asp Met Pro Val Ala His Val
1               5                  10                 15 gta gca aac cct caa gct gag ggg cag ctc cag tgg ctg aac cgc cgg      96
Val Ala Asn Pro Gln Ala Glu Gly Gln Leu Gln Trp Leu Asn Arg Arg
            20                  25                  30 gcc aat gcc ctc ctg gcc aat ggc gtg gag ctg aga gat aac cag ctg     144
Ala Asn Ala Leu Leu Ala Asn Gly Val Glu Leu Arg Asp Asn Gln Leu
        35                  40                  45 gtg gtg cca tca gag ggc ctg tac ctc atc tac tcc cag gtc ctc ttc     192
Val Val Pro Ser Glu Gly Leu Tyr Leu Ile Tyr Ser Gln Val Leu Phe
```

```
                  50                  55                  60
tcg ggc caa ggc tgc ccc tcc acc cat gtg ctc ctc acc cac acc atc        240
Ser Gly Gln Gly Cys Pro Ser Thr His Val Leu Leu Thr His Thr Ile
 65                  70                  75                  80 agc cgc atc tcc ccc ctg tac ccc aag ccc gtc aac ctc ctc tct gcc        288
Ser Arg Ile Ser Pro Leu Tyr Pro Lys Pro Val Asn Leu Leu Ser Ala
                 85                  90                  95 atc cgc agc ccc tgc cag agg gag acc cca gag ggg gct gag gcc aac        336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg        384
Pro Trp Tyr Glu Pro Ile Tyr Leu Gly Gly Val Phe Gln Leu Glu Pro
        115                 120                 125 ggt gac cga ctc agc gct gag atc aat cgg ccc gac tat ctc gac ttt        432
Gly Asp Arg Leu Ser Ala Glu Ile Asn Arg Pro Asp Tyr Leu Asp Phe
130                 135                 140 gcc gag tct ggg cag gtc tac ttt ggg atc att gcc ctg                    471
Ala Glu Ser Gly Gln Val Tyr Phe Gly Ile Ile Ala Leu
145                 150                 155

<210> SEQ ID NO 67
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 19
<220> FEATURE:
<221> NAME/KEY: CDS
<222> LOCATION: (1)..(471)

<400> SEQUENCE: 67 gtc aga tca tct tct cga acc ccg agt gac atg cct gta gcc cat gtt         48
Val Arg Ser Ser Ser Arg Thr Pro Ser Asp Met Pro Val Ala His Val
  1               5                  10                  15 gta gca aac cct caa gct gag ggg cag ctc cag tgg ctg aac cgc cgg         96
Val Ala Asn Pro Gln Ala Glu Gly Gln Leu Gln Trp Leu Asn Arg Arg
             20                  25                  30 gcc aat gcc ctc ctg gcc aat ggc gtg gag ctg aga gat aac cag ctg        144
Ala Asn Ala Leu Leu Ala Asn Gly Val Glu Leu Arg Asp Asn Gln Leu
         35                  40                  45 gtg gtg cca tca gag ggc ctg tac ctc atc tac tcc cag gtc ctc ttc        192
Val Val Pro Ser Glu Gly Leu Tyr Leu Ile Tyr Ser Gln Val Leu Phe
     50                  55                  60 tcg ggc caa ggc tgc ccc tcc acc cat gtg ctc ctc acc cac acc atc        240
Ser Gly Gln Gly Cys Pro Ser Thr His Val Leu Leu Thr His Thr Ile
 65                  70                  75                  80 agc cgc atc tcc acc aac tac aac ggc ccc gtc aac ctc ctc tct gcc        288
Ser Arg Ile Ser Thr Asn Tyr Asn Gly Pro Val Asn Leu Leu Ser Ala
                 85                  90                  95 atc cgc agc ccc tgc cag agg gag acc cca gag ggg gct gag gcc aac        336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg        384
Pro Trp Tyr Glu Pro Ile Tyr Leu Gly Gly Val Phe Gln Leu Glu Pro
        115                 120                 125 ggt gac cga ctc agc gct gag atc aat cgg ccc gac tat ctc gac ttt        432
Gly Asp Arg Leu Ser Ala Glu Ile Asn Arg Pro Asp Tyr Leu Asp Phe
130                 135                 140 gcc gag tct ggg cag gtc tac ttt ggg atc att gcc ctg                    471
Ala Glu Ser Gly Gln Val Tyr Phe Gly Ile Ile Ala Leu
145                 150                 155
```

<210> SEQ ID NO 68
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 20
<220> FEATURE:
<221> NAME/KEY: CDS
<222> LOCATION: (1)..(471)

<400> SEQUENCE: 68

```
gtc aga tca tct tct cga acc ccg agt gac atg cct gta gcc cat gtt      48
Val Arg Ser Ser Ser Arg Thr Pro Ser Asp Met Pro Val Ala His Val
1               5                   10                  15 gta gca aac cct caa gct gag ggg cag ctc cag tgg ctg aac cgc cgg      96
Val Ala Asn Pro Gln Ala Glu Gly Gln Leu Gln Trp Leu Asn Arg Arg
            20                  25                  30 gcc aat gcc ctc ctg gcc aat ggc gtg gag ctg aga gat aac cag ctg     144
Ala Asn Ala Leu Leu Ala Asn Gly Val Glu Leu Arg Asp Asn Gln Leu
        35                  40                  45 gtg gtg cca tca gag ggc ctg tac ctc atc tac tcc cag gtc ctc ttc     192
Val Val Pro Ser Glu Gly Leu Tyr Leu Ile Tyr Ser Gln Val Leu Phe
    50                  55                  60 tcg ggc caa ggc tgc ccc tcc acc cat gtg ctc ctc acc cac acc atc     240
Ser Gly Gln Gly Cys Pro Ser Thr His Val Leu Leu Thr His Thr Ile
65                  70                  75                  80 agc cgc atc tcc agc gcg tac gcg agc ccc gtc aac ctc ctc tct gcc     288
Ser Arg Ile Ser Ser Ala Tyr Ala Ser Pro Val Asn Leu Leu Ser Ala
                85                  90                  95 atc cgc agc ccc tgc cag agg gag acc cca gag ggg gct gag gcc aac     336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg     384
Pro Trp Tyr Glu Pro Ile Tyr Leu Gly Gly Val Phe Gln Leu Glu Pro
        115                 120                 125 ggt gac cga ctc agc gct gag atc aat cgg ccc gac tat ctc gac ttt     432
Gly Asp Arg Leu Ser Ala Glu Ile Asn Arg Pro Asp Tyr Leu Asp Phe
    130                 135                 140 gcc gag tct ggg cag gtc tac ttt ggg atc att gcc ctg                 471
Ala Glu Ser Gly Gln Val Tyr Phe Gly Ile Ile Ala Leu
145                 150                 155
```

<210> SEQ ID NO 69
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 21
<220> FEATURE:
<221> NAME/KEY: CDS
<222> LOCATION: (1)..(471)

<400> SEQUENCE: 69

```
gtc aga tca tct tct cga acc ccg agt gac atg cct gta gcc cat gtt      48
Val Arg Ser Ser Ser Arg Thr Pro Ser Asp Met Pro Val Ala His Val
1               5                   10                  15 gta gca aac cct caa gct gag ggg cag ctc cag tgg ctg aac cgc cgg      96
Val Ala Asn Pro Gln Ala Glu Gly Gln Leu Gln Trp Leu Asn Arg Arg
```

```
                 20                  25                  30
gcc aat gcc ctc ctg gcc aat ggc gtg gag ctg aga gat aac cag ctg      144
Ala Asn Ala Leu Leu Ala Asn Gly Val Glu Leu Arg Asp Asn Gln Leu
             35                  40                  45 gtg gtg cca tca gag ggc ctg tac ctc atc tac tcc cag gtc ctc ttc      192
Val Val Pro Ser Glu Gly Leu Tyr Leu Ile Tyr Ser Gln Val Leu Phe
 50                  55                  60 tcg ggc caa ggc tgc ccc tcc acc cat gtg ctc ctc acc cac acc atc      240
Ser Gly Gln Gly Cys Pro Ser Thr His Val Leu Leu Thr His Thr Ile
 65                  70                  75                  80 agc cgc atc tcg tcg gcc tac ggg ccg ccc gtc aac ctc ctc tct gcc      288
Ser Arg Ile Ser Ser Ala Tyr Gly Pro Pro Val Asn Leu Leu Ser Ala
                 85                  90                  95 atc cgc agc ccc tgc cag agg gag acc cca gag ggg gct gag gcc aac      336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg      384
Pro Trp Tyr Glu Pro Ile Tyr Leu Gly Gly Val Phe Gln Leu Glu Pro
            115                 120                 125 ggt gac cga ctc agc gct gag atc aat cgg ccc gac tat ctc gac ttt      432
Gly Asp Arg Leu Ser Ala Glu Ile Asn Arg Pro Asp Tyr Leu Asp Phe
130                 135                 140 gcc gag tct ggg cag gtc tac ttt ggg atc att gcc ctg                  471
Ala Glu Ser Gly Gln Val Tyr Phe Gly Ile Ile Ala Leu
145                 150                 155

<210> SEQ ID NO 70
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 22
<220> FEATURE:
<221> NAME/KEY: CDS
<222> LOCATION: (1)..(471)

<400> SEQUENCE: 70 gtc aga tca tct tct cga acc ccg agt gac atg cct gta gcc cat gtt       48
Val Arg Ser Ser Ser Arg Thr Pro Ser Asp Met Pro Val Ala His Val
 1               5                  10                  15 gta gca aac cct caa gct gag ggg cag ctc cag tgg ctg aac cgc cgg       96
Val Ala Asn Pro Gln Ala Glu Gly Gln Leu Gln Trp Leu Asn Arg Arg
                 20                  25                  30 gcc aat gcc ctc ctg gcc aat ggc gtg gag ctg aga gat aac cag ctg      144
Ala Asn Ala Leu Leu Ala Asn Gly Val Glu Leu Arg Asp Asn Gln Leu
             35                  40                  45 gtg gtg cca tca gag ggc ctg tac ctc atc tac tcc cag gtc ctc ttc      192
Val Val Pro Ser Glu Gly Leu Tyr Leu Ile Tyr Ser Gln Val Leu Phe
 50                  55                  60 tcg ggc caa ggc tgc ccc tcc acc cat gtg ctc ctc acc cac acc atc      240
Ser Gly Gln Gly Cys Pro Ser Thr His Val Leu Leu Thr His Thr Ile
 65                  70                  75                  80 agc cgc atc tcg cgc gtg tac acc gcc ccc gtc aac ctc ctc tct gcc      288
Ser Arg Ile Ser Arg Val Tyr Thr Ala Pro Val Asn Leu Leu Ser Ala
                 85                  90                  95 atc cgc agc ccc tgc cag agg gag acc cca gag ggg gct gag gcc aac      336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg      384
Pro Trp Tyr Glu Pro Ile Tyr Leu Gly Gly Val Phe Gln Leu Glu Pro
```

```
                     115                 120                 125
ggt gac cga ctc agc gct gag atc aat cgg ccc gac tat ctc gac ttt        432
Gly Asp Arg Leu Ser Ala Glu Ile Asn Arg Pro Asp Tyr Leu Asp Phe
    130                 135                 140 gcc gag tct ggg cag gtc tac ttt ggg atc att gcc ctg                    471
Ala Glu Ser Gly Gln Val Tyr Phe Gly Ile Ile Ala Leu
145                 150                 155

<210> SEQ ID NO 71
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 23
<220> FEATURE:
<221> NAME/KEY: CDS
<222> LOCATION: (1)..(471)

<400> SEQUENCE: 71 gtc aga tca tct tct cga acc ccg agt gac atg cct gta gcc cat gtt         48
Val Arg Ser Ser Ser Arg Thr Pro Ser Asp Met Pro Val Ala His Val
1               5                   10                  15 gta gca aac cct caa gct gag ggg cag ctc cag tgg ctg aac cgc cgg         96
Val Ala Asn Pro Gln Ala Glu Gly Gln Leu Gln Trp Leu Asn Arg Arg
            20                  25                  30 gcc aat gcc ctc ctg gcc aat ggc gtg gag ctg aga gat aac cag ctg        144
Ala Asn Ala Leu Leu Ala Asn Gly Val Glu Leu Arg Asp Asn Gln Leu
        35                  40                  45 gtg gtg cca tca gag ggc ctg tac ctc atc tac tcc cag gtc ctc ttc        192
Val Val Pro Ser Glu Gly Leu Tyr Leu Ile Tyr Ser Gln Val Leu Phe
    50                  55                  60 tcg ggc caa ggc tgc ccc tcc acc cat gtg ctc ctc acc cac acc atc        240
Ser Gly Gln Gly Cys Pro Ser Thr His Val Leu Leu Thr His Thr Ile
65                  70                  75                  80 agc cgc atc acg acg gcg tac agc ggc ccc gtc aac ctc ctc tct gcc        288
Ser Arg Ile Thr Thr Ala Tyr Ser Gly Pro Val Asn Leu Leu Ser Ala
                85                  90                  95 atc cgc agc ccc tgc cag agg gag acc cca gag ggg gct gag gcc aac        336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg        384
Pro Trp Tyr Glu Pro Ile Tyr Leu Gly Gly Val Phe Gln Leu Glu Pro
        115                 120                 125 ggt gac cga ctc agc gct gag atc aat cgg ccc gac tat ctc gac ttt        432
Gly Asp Arg Leu Ser Ala Glu Ile Asn Arg Pro Asp Tyr Leu Asp Phe
    130                 135                 140 gcc gag tct ggg cag gtc tac ttt ggg atc att gcc ctg                    471
Ala Glu Ser Gly Gln Val Tyr Phe Gly Ile Ile Ala Leu
145                 150                 155

<210> SEQ ID NO 72
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 24
<220> FEATURE:
<221> NAME/KEY: CDS
<222> LOCATION: (1)..(471)
```

-continued

```
<400> SEQUENCE: 72 gtc aga tca tct tct cga acc ccg agt gac atg cct gta gcc cat gtt       48
Val Arg Ser Ser Ser Arg Thr Pro Ser Asp Met Pro Val Ala His Val
1               5                   10                  15 gta gca aac cct caa gct gag ggg cag ctc cag tgg ctg aac cgc cgg       96
Val Ala Asn Pro Gln Ala Glu Gly Gln Leu Gln Trp Leu Asn Arg Arg
            20                  25                  30 gcc aat gcc ctc ctg gcc aat ggc gtg gag ctg aga gat aac cag ctg      144
Ala Asn Ala Leu Leu Ala Asn Gly Val Glu Leu Arg Asp Asn Gln Leu
        35                  40                  45 gtg gtg cca tca gag ggc ctg tac ctc atc tac tcc cag gtc ctc ttc      192
Val Val Pro Ser Glu Gly Leu Tyr Leu Ile Tyr Ser Gln Val Leu Phe
    50                  55                  60 tcg ggc caa ggc tgc ccc tcc acc cat gtg ctc ctc acc cac acc atc      240
Ser Gly Gln Gly Cys Pro Ser Thr His Val Leu Leu Thr His Thr Ile
65                  70                  75                  80 agc cgc atc acg cac aag tac ccg cag ccc gtc aac ctc ctc tct gcc      288
Ser Arg Ile Thr His Lys Tyr Pro Gln Pro Val Asn Leu Leu Ser Ala
                85                  90                  95 atc cgc agc ccc tgc cag agg gag acc cca gag ggg gct gag gcc aac      336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg      384
Pro Trp Tyr Glu Pro Ile Tyr Leu Gly Gly Val Phe Gln Leu Glu Pro
        115                 120                 125 ggt gac cga ctc agc gct gag atc aat cgg ccc gac tat ctc gac ttt      432
Gly Asp Arg Leu Ser Ala Glu Ile Asn Arg Pro Asp Tyr Leu Asp Phe
    130                 135                 140 gcc gag tct ggg cag gtc tac ttt ggg atc att gcc ctg                  471
Ala Glu Ser Gly Gln Val Tyr Phe Gly Ile Ile Ala Leu
145                 150                 155

<210> SEQ ID NO 73
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 25
<220> FEATURE:
<221> NAME/KEY: CDS
<222> LOCATION: (1)..(471)

<400> SEQUENCE: 73 gtc aga tca tct tct cga acc ccg agt gac atg cct gta gcc cat gtt       48
Val Arg Ser Ser Ser Arg Thr Pro Ser Asp Met Pro Val Ala His Val
1               5                   10                  15 gta gca aac cct caa gct gag ggg cag ctc cag tgg ctg aac cgc cgg       96
Val Ala Asn Pro Gln Ala Glu Gly Gln Leu Gln Trp Leu Asn Arg Arg
            20                  25                  30 gcc aat gcc ctc ctg gcc aat ggc gtg gag ctg aga gat aac cag ctg      144
Ala Asn Ala Leu Leu Ala Asn Gly Val Glu Leu Arg Asp Asn Gln Leu
        35                  40                  45 gtg gtg cca tca gag ggc ctg tac ctc atc tac tcc cag gtc ctc ttc      192
Val Val Pro Ser Glu Gly Leu Tyr Leu Ile Tyr Ser Gln Val Leu Phe
    50                  55                  60 tcg ggc caa ggc tgc ccc tcc acc cat gtg ctc ctc acc cac acc atc      240
Ser Gly Gln Gly Cys Pro Ser Thr His Val Leu Leu Thr His Thr Ile
65                  70                  75                  80 agc cgc atc agc aag acc tac tcc cac ccc gtc aac ctc ctc tct gcc      288
Ser Arg Ile Ser Lys Thr Tyr Ser His Pro Val Asn Leu Leu Ser Ala
```

```
atc cgc agc ccc tgc cag agg gag acc cca gag ggg gct gag gcc aac        336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg        384
Pro Trp Tyr Glu Pro Ile Tyr Leu Gly Gly Val Phe Gln Leu Glu Pro
            115                 120                 125 ggt gac cga ctc agc gct gag atc aat cgg ccc gac tat ctc gac ttt        432
Gly Asp Arg Leu Ser Ala Glu Ile Asn Arg Pro Asp Tyr Leu Asp Phe
        130                 135                 140 gcc gag tct ggg cag gtc tac ttt ggg atc att gcc ctg                    471
Ala Glu Ser Gly Gln Val Tyr Phe Gly Ile Ile Ala Leu
145                 150                 155

<210> SEQ ID NO 74
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 26
<220> FEATURE:
<221> NAME/KEY: CDS
<222> LOCATION: (1)..(471)

<400> SEQUENCE: 74 gtc aga tca tct tct cga acc ccg agt gac atg cct gta gcc cat gtt        48
Val Arg Ser Ser Ser Arg Thr Pro Ser Asp Met Pro Val Ala His Val
1               5                   10                  15 gta gca aac cct caa gct gag ggg cag ctc cag tgg ctg aac cgc cgg        96
Val Ala Asn Pro Gln Ala Glu Gly Gln Leu Gln Trp Leu Asn Arg Arg
            20                  25                  30 gcc aat gcc ctc ctg gcc aat ggc gtg gag ctg aga gat aac cag ctg        144
Ala Asn Ala Leu Leu Ala Asn Gly Val Glu Leu Arg Asp Asn Gln Leu
        35                  40                  45 gtg gtg cca tca gag ggc ctg tac ctc atc tac tcc cag gtc ctc ttc        192
Val Val Pro Ser Glu Gly Leu Tyr Leu Ile Tyr Ser Gln Val Leu Phe
    50                  55                  60 tcg ggc caa ggc tgc ccc tcc acc cat gtg ctc ctc acc cac acc atc        240
Ser Gly Gln Gly Cys Pro Ser Thr His Val Leu Leu Thr His Thr Ile
65                  70                  75                  80 agc cgc atc tcg tcc cac tac agg ttc ccc gtc aac ctc ctc tct gcc        288
Ser Arg Ile Ser Ser His Tyr Arg Phe Pro Val Asn Leu Leu Ser Ala
            85                  90                  95 atc cgc agc ccc tgc cag agg gag acc cca gag ggg gct gag gcc aac        336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg        384
Pro Trp Tyr Glu Pro Ile Tyr Leu Gly Gly Val Phe Gln Leu Glu Pro
            115                 120                 125 ggt gac cga ctc agc gct gag atc aat cgg ccc gac tat ctc gac ttt        432
Gly Asp Arg Leu Ser Ala Glu Ile Asn Arg Pro Asp Tyr Leu Asp Phe
        130                 135                 140 gcc gag tct ggg cag gtc tac ttt ggg atc att gcc ctg                    471
Ala Glu Ser Gly Gln Val Tyr Phe Gly Ile Ile Ala Leu
145                 150                 155

<210> SEQ ID NO 75
<211> LENGTH: 471
<212> TYPE: DNA
<213> ORGANISM: Artificial Sequence
<220> FEATURE:
```

-continued

```
<223> OTHER INFORMATION: Synthetic
<220> FEATURE:
<221> NAME/KEY: misc_feature
<223> OTHER INFORMATION: Clone No. 27
<220> FEATURE:
<221> NAME/KEY: CDS
<222> LOCATION: (1)..(471)

<400> SEQUENCE: 75 gtc aga tca tct tct cga acc ccg agt gac atg cct gta gcc cat gtt      48
Val Arg Ser Ser Ser Arg Thr Pro Ser Asp Met Pro Val Ala His Val
1               5                   10                  15 gta gca aac cct caa gct gag ggg cag ctc cag tgg ctg aac cgc cgg      96
Val Ala Asn Pro Gln Ala Glu Gly Gln Leu Gln Trp Leu Asn Arg Arg
                20                  25                  30 gcc aat gcc ctc ctg gcc aat ggc gtg gag ctg aga gat aac cag ctg     144
Ala Asn Ala Leu Leu Ala Asn Gly Val Glu Leu Arg Asp Asn Gln Leu
            35                  40                  45 gtg gtg cca tca gag ggc ctg tac ctc atc tac tcc cag gtc ctc ttc     192
Val Val Pro Ser Glu Gly Leu Tyr Leu Ile Tyr Ser Gln Val Leu Phe
    50                  55                  60 tcg ggc caa ggc tgc ccc tcc acc cat gtg ctc ctc acc cac acc atc     240
Ser Gly Gln Gly Cys Pro Ser Thr His Val Leu Leu Thr His Thr Ile
65                  70                  75                  80 agc cgc atc acc ccc gcc tac ccc cgg ccc gtc aac ctc ctc tct gcc     288
Ser Arg Ile Thr Pro Ala Tyr Pro Arg Pro Val Asn Leu Leu Ser Ala
                85                  90                  95 atc cgc agc ccc tgc cag agg gag acc cca gag ggg gct gag gcc aac     336
Ile Arg Ser Pro Cys Gln Arg Glu Thr Pro Glu Gly Ala Glu Ala Asn
                100                 105                 110 ccc tgg tat gag ccc atc tat ctg gga ggg gtc ttc cag ctg gag ccg     384
Pro Trp Tyr Glu Pro Ile Tyr Leu Gly Gly Val Phe Gln Leu Glu Pro
            115                 120                 125 ggt gac cga ctc agc gct gag atc aat cgg ccc gac tat ctc gac ttt     432
Gly Asp Arg Leu Ser Ala Glu Ile Asn Arg Pro Asp Tyr Leu Asp Phe
    130                 135                 140 gcc gag tct ggg cag gtc tac ttt ggg atc att gcc ctg                 471
Ala Glu Ser Gly Gln Val Tyr Phe Gly Ile Ile Ala Leu
145                 150                 155

<210> SEQ ID NO 76
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 28
<220> FEATURE:
<221> NAME/KEY: CDS
<222> LOCATION: (1)..(471)

<400> SEQUENCE: 76 gtc aga tca tct tct cga acc ccg agt gac atg cct gta gcc cat gtt      48
Val Arg Ser Ser Ser Arg Thr Pro Ser Asp Met Pro Val Ala His Val
1               5                   10                  15 gta gca aac cct caa gct gag ggg cag ctc cag tgg ctg aac cgc cgg      96
Val Ala Asn Pro Gln Ala Glu Gly Gln Leu Gln Trp Leu Asn Arg Arg
                20                  25                  30 gcc aat gcc ctc ctg gcc aat ggc gtg gag ctg aga gat aac cag ctg     144
Ala Asn Ala Leu Leu Ala Asn Gly Val Glu Leu Arg Asp Asn Gln Leu
            35                  40                  45 gtg gtg cca tca gag ggc ctg tac ctc atc tac tcc cag gtc ctc ttc     192
Val Val Pro Ser Glu Gly Leu Tyr Leu Ile Tyr Ser Gln Val Leu Phe
```

```
tcg ggc caa ggc tgc ccc tcc acc cat gtg ctc ctc acc cac acc atc    240
Ser Gly Gln Gly Cys Pro Ser Thr His Val Leu Leu Thr His Thr Ile
 65                  70                  75                  80 agc cgc atc acg aag tcc tac tcc aag ccc gtc aac ctc ctc tct gcc    288
Ser Arg Ile Thr Lys Ser Tyr Ser Lys Pro Val Asn Leu Leu Ser Ala
                 85                  90                  95 atc cgc agc ccc tgc cag agg gag acc cca gag ggg gct gag gcc aac    336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg    384
Pro Trp Tyr Glu Pro Ile Tyr Leu Gly Gly Val Phe Gln Leu Glu Pro
        115                 120                 125 ggt gac cga ctc agc gct gag atc aat cgg ccc gac tat ctc gac ttt    432
Gly Asp Arg Leu Ser Ala Glu Ile Asn Arg Pro Asp Tyr Leu Asp Phe
130                 135                 140 gcc gag tct ggg cag gtc tac ttt ggg atc att gcc ctg                471
Ala Glu Ser Gly Gln Val Tyr Phe Gly Ile Ile Ala Leu
145                 150                 155

<210> SEQ ID NO 77
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 29
<220> FEATURE:
<221> NAME/KEY: CDS
<222> LOCATION: (1)..(471)

<400> SEQUENCE: 77 gtc aga tca tct tct cga acc ccg agt gac atg cct gta gcc cat gtt     48
Val Arg Ser Ser Ser Arg Thr Pro Ser Asp Met Pro Val Ala His Val
 1               5                  10                  15 gta gca aac cct caa gct gag ggg cag ctc cag tgg ctg aac cgc cgg     96
Val Ala Asn Pro Gln Ala Glu Gly Gln Leu Gln Trp Leu Asn Arg Arg
             20                  25                  30 gcc aat gcc ctc ctg gcc aat ggc gtg gag ctg aga gat aac cag ctg    144
Ala Asn Ala Leu Leu Ala Asn Gly Val Glu Leu Arg Asp Asn Gln Leu
         35                  40                  45 gtg gtg cca tca gag ggc ctg tac ctc atc tac tcc cag gtc ctc ttc    192
Val Val Pro Ser Glu Gly Leu Tyr Leu Ile Tyr Ser Gln Val Leu Phe
     50                  55                  60 tcg ggc caa ggc tgc ccc tcc acc cat gtg ctc ctc acc cac acc atc    240
Ser Gly Gln Gly Cys Pro Ser Thr His Val Leu Leu Thr His Thr Ile
 65                  70                  75                  80 agc cgc atc acc gag cag tac tcc cac ccc gtc aac ctc ctc tct gcc    288
Ser Arg Ile Thr Glu Gln Tyr Ser His Pro Val Asn Leu Leu Ser Ala
                 85                  90                  95 atc cgc agc ccc tgc cag agg gag acc cca gag ggg gct gag gcc aac    336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg    384
Pro Trp Tyr Glu Pro Ile Tyr Leu Gly Gly Val Phe Gln Leu Glu Pro
        115                 120                 125 ggt gac cga ctc agc gct gag atc aat cgg ccc gac tat ctc gac ttt    432
Gly Asp Arg Leu Ser Ala Glu Ile Asn Arg Pro Asp Tyr Leu Asp Phe
130                 135                 140 gcc gag tct ggg cag gtc tac ttt ggg atc att gcc ctg                471
Ala Glu Ser Gly Gln Val Tyr Phe Gly Ile Ile Ala Leu
145                 150                 155
```

<210> SEQ ID NO 78
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 30
<220> FEATURE:
<221> NAME/KEY: CDS
<222> LOCATION: (1)..(471)

<400> SEQUENCE: 78

```
gtc aga tca tct tct cga acc ccg agt gac atg cct gta gcc cat gtt       48
Val Arg Ser Ser Ser Arg Thr Pro Ser Asp Met Pro Val Ala His Val
 1               5                  10                  15 gta gca aac cct caa gct gag ggg cag ctc cag tgg ctg aac cgc cgg       96
Val Ala Asn Pro Gln Ala Glu Gly Gln Leu Gln Trp Leu Asn Arg Arg
             20                  25                  30 gcc aat gcc ctc ctg gcc aat ggc gtg gag ctg aga gat aac cag ctg      144
Ala Asn Ala Leu Leu Ala Asn Gly Val Glu Leu Arg Asp Asn Gln Leu
         35                  40                  45 gtg gtg cca tca gag ggc ctg tac ctc atc tac tcc cag gtc ctc ttc      192
Val Val Pro Ser Glu Gly Leu Tyr Leu Ile Tyr Ser Gln Val Leu Phe
     50                  55                  60 tcg ggc caa ggc tgc ccc tcc acc cat gtg ctc ctc acc cac acc atc      240
Ser Gly Gln Gly Cys Pro Ser Thr His Val Leu Leu Thr His Thr Ile
 65                  70                  75                  80 agc cgc atc acg ccc cag tac ccg tcc ccc gtc aac ctc ctc tct gcc      288
Ser Arg Ile Thr Pro Gln Tyr Pro Ser Pro Val Asn Leu Leu Ser Ala
                 85                  90                  95 atc cgc agc ccc tgc cag agg gag acc cca gag ggg gct gag gcc aac      336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg      384
Pro Trp Tyr Glu Pro Ile Tyr Leu Gly Gly Val Phe Gln Leu Glu Pro
        115                 120                 125 ggt gac cga ctc agc gct gag atc aat cgg ccc gac tat ctc gac ttt      432
Gly Asp Arg Leu Ser Ala Glu Ile Asn Arg Pro Asp Tyr Leu Asp Phe
    130                 135                 140 gcc gag tct ggg cag gtc tac ttt ggg atc att gcc ctg                  471
Ala Glu Ser Gly Gln Val Tyr Phe Gly Ile Ile Ala Leu
145                 150                 155
```

<210> SEQ ID NO 79
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 31
<220> FEATURE:
<221> NAME/KEY: CDS
<222> LOCATION: (1)..(471)

<400> SEQUENCE: 79

```
gtc aga tca tct tct cga acc ccg agt gac atg cct gta gcc cat gtt       48
Val Arg Ser Ser Ser Arg Thr Pro Ser Asp Met Pro Val Ala His Val
 1               5                  10                  15 gta gca aac cct caa gct gag ggg cag ctc cag tgg ctg aac cgc cgg       96
Val Ala Asn Pro Gln Ala Glu Gly Gln Leu Gln Trp Leu Asn Arg Arg
             20                  25                  30
```

```
                     20                   25                   30
gcc aat gcc ctc ctg gcc aat ggc gtg gag ctg aga gat aac cag ctg        144
Ala Asn Ala Leu Leu Ala Asn Gly Val Glu Leu Arg Asp Asn Gln Leu
             35                  40                  45 gtg gtg cca tca gag ggc ctg tac ctc atc tac tcc cag gtc ctc ttc        192
Val Val Pro Ser Glu Gly Leu Tyr Leu Ile Tyr Ser Gln Val Leu Phe
 50                  55                  60 tcg ggc caa ggc tgc ccc tcc acc cat gtg ctc ctc acc cac acc atc        240
Ser Gly Gln Gly Cys Pro Ser Thr His Val Leu Leu Thr His Thr Ile
 65                  70                  75                  80 agc cgc atc agc aag acc tac tcc cac ccc gtc aac ctc ctc tct gcc        288
Ser Arg Ile Ser Lys Thr Tyr Ser His Pro Val Asn Leu Leu Ser Ala
                 85                  90                  95 atc cgc agc ccc tgc cag agg gag acc cca gag ggg gct gag gcc aac        336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg        384
Pro Trp Tyr Glu Pro Ile Tyr Leu Gly Gly Val Phe Gln Leu Glu Pro
        115                 120                 125 ggt gac cga ctc agc gct gag atc aat cgg ccc gac tat ctc gac ttt        432
Gly Asp Arg Leu Ser Ala Glu Ile Asn Arg Pro Asp Tyr Leu Asp Phe
130                 135                 140 gcc gag tct ggg cag gtc tac ttt ggg atc att gcc ctg                    471
Ala Glu Ser Gly Gln Val Tyr Phe Gly Ile Ile Ala Leu
145                 150                 155

<210> SEQ ID NO 80
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 32
<220> FEATURE:
<221> NAME/KEY: CDS
<222> LOCATION: (1)..(471)

<400> SEQUENCE: 80 gtc aga tca tct tct cga acc ccg agt gac atg cct gta gcc cat gtt         48
Val Arg Ser Ser Ser Arg Thr Pro Ser Asp Met Pro Val Ala His Val
 1               5                  10                  15 gta gca aac cct caa gct gag ggg cag ctc cag tgg ctg aac cgc cgg         96
Val Ala Asn Pro Gln Ala Glu Gly Gln Leu Gln Trp Leu Asn Arg Arg
             20                  25                  30 gcc aat gcc ctc ctg gcc aat ggc gtg gag ctg aga gat aac cag ctg        144
Ala Asn Ala Leu Leu Ala Asn Gly Val Glu Leu Arg Asp Asn Gln Leu
             35                  40                  45 gtg gtg cca tca gag ggc ctg tac ctc atc tac tcc cag gtc ctc ttc        192
Val Val Pro Ser Glu Gly Leu Tyr Leu Ile Tyr Ser Gln Val Leu Phe
 50                  55                  60 tcg ggc caa ggc tgc ccc tcc acc cat gtg ctc ctc acc cac acc atc        240
Ser Gly Gln Gly Cys Pro Ser Thr His Val Leu Leu Thr His Thr Ile
 65                  70                  75                  80 agc cgc atc acg gac cgc tac agc agc ccc gtc aac ctc ctc tct gcc        288
Ser Arg Ile Thr Asp Arg Tyr Ser Ser Pro Val Asn Leu Leu Ser Ala
                 85                  90                  95 atc cgc agc ccc tgc cag agg gag acc cca gag ggg gct gag gcc aac        336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg        384
Pro Trp Tyr Glu Pro Ile Tyr Leu Gly Gly Val Phe Gln Leu Glu Pro
```

```
ggt gac cga ctc agc gct gag atc aat cgg ccc gac tat ctc gac ttt      432
Gly Asp Arg Leu Ser Ala Glu Ile Asn Arg Pro Asp Tyr Leu Asp Phe
    130                 135                 140 gcc gag tct ggg cag gtc tac ttt ggg atc att gcc ctg                  471
Ala Glu Ser Gly Gln Val Tyr Phe Gly Ile Ile Ala Leu
145                 150                 155
```

```
<210> SEQ ID NO 81
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 33
<220> FEATURE:
<221> NAME/KEY: CDS
<222> LOCATION: (1)..(471)

<400> SEQUENCE: 81 gtc aga tca tct tct cga acc ccg agt gac atg cct gta gcc cat gtt      48
Val Arg Ser Ser Ser Arg Thr Pro Ser Asp Met Pro Val Ala His Val
1               5                   10                  15 gta gca aac cct caa gct gag ggg cag ctc cag tgg ctg aac cgc cgg      96
Val Ala Asn Pro Gln Ala Glu Gly Gln Leu Gln Trp Leu Asn Arg Arg
            20                  25                  30 gcc aat gcc ctc ctg gcc aat ggc gtg gag ctg aga gat aac cag ctg     144
Ala Asn Ala Leu Leu Ala Asn Gly Val Glu Leu Arg Asp Asn Gln Leu
        35                  40                  45 gtg gtg cca tca gag ggc ctg tac ctc atc tac tcc cag gtc ctc ttc     192
Val Val Pro Ser Glu Gly Leu Tyr Leu Ile Tyr Ser Gln Val Leu Phe
    50                  55                  60 tcg ggc caa ggc tgc ccc tcc acc cat gtg ctc ctc acc cac acc atc     240
Ser Gly Gln Gly Cys Pro Ser Thr His Val Leu Leu Thr His Thr Ile
65                  70                  75                  80 agc cgc atc aac cac agg tac cag gac ccc gtc aac ctc ctc tct gcc     288
Ser Arg Ile Asn His Arg Tyr Gln Asp Pro Val Asn Leu Leu Ser Ala
                85                  90                  95 atc cgc agc ccc tgc cag agg gag acc cca gag ggg gct gag gcc aac     336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg     384
Pro Trp Tyr Glu Pro Ile Tyr Leu Gly Gly Val Phe Gln Leu Glu Pro
        115                 120                 125 ggt gac cga ctc agc gct gag atc aat cgg ccc gac tat ctc gac ttt     432
Gly Asp Arg Leu Ser Ala Glu Ile Asn Arg Pro Asp Tyr Leu Asp Phe
    130                 135                 140 gcc gag tct ggg cag gtc tac ttt ggg atc att gcc ctg                  471
Ala Glu Ser Gly Gln Val Tyr Phe Gly Ile Ile Ala Leu
145                 150                 155

<210> SEQ ID NO 82
<211> LENGTH: 471
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Clone No. 34
<220> FEATURE:
<221> NAME/KEY: CDS
<222> LOCATION: (1)..(471)
```

-continued

```
<400> SEQUENCE: 82 gtc aga tca tct tct cga acc ccg agt gac atg cct gta gcc cat gtt      48
Val Arg Ser Ser Ser Arg Thr Pro Ser Asp Met Pro Val Ala His Val
1               5                   10                  15 gta gca aac cct caa gct gag ggg cag ctc cag tgg ctg aac cgc cgg      96
Val Ala Asn Pro Gln Ala Glu Gly Gln Leu Gln Trp Leu Asn Arg Arg
            20                  25                  30 gcc aat gcc ctc ctg gcc aat ggc gtg gag ctg aga gat aac cag ctg     144
Ala Asn Ala Leu Leu Ala Asn Gly Val Glu Leu Arg Asp Asn Gln Leu
        35                  40                  45 gtg gtg cca tca gag ggc ctg tac ctc atc tac tcc cag gtc ctc ttc     192
Val Val Pro Ser Glu Gly Leu Tyr Leu Ile Tyr Ser Gln Val Leu Phe
    50                  55                  60 tcg ggc caa ggc tgc ccc tcc acc cat gtg ctc ctc acc cac acc atc     240
Ser Gly Gln Gly Cys Pro Ser Thr His Val Leu Leu Thr His Thr Ile
65                  70                  75                  80 agc cgc atc tcc gcg gac tac ccc cac ccc gtc aac ctc ctc tct gcc     288
Ser Arg Ile Ser Ala Asp Tyr Pro His Pro Val Asn Leu Leu Ser Ala
                85                  90                  95 atc cgc agc ccc tgc cag agg gag acc cca gag ggg gct gag gcc aac     336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg     384
Pro Trp Tyr Glu Pro Ile Tyr Leu Gly Gly Val Phe Gln Leu Glu Pro
        115                 120                 125 ggt gac cga ctc agc gct gag atc aat cgg ccc gac tat ctc gac ttt     432
Gly Asp Arg Leu Ser Ala Glu Ile Asn Arg Pro Asp Tyr Leu Asp Phe
    130                 135                 140 gcc gag tct ggg cag gtc tac ttt ggg atc att gcc ctg              471
Ala Glu Ser Gly Gln Val Tyr Phe Gly Ile Ile Ala Leu
145                 150                 155

<210> SEQ ID NO 83
<211> LENGTH: 87
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(32)
<223> OTHER INFORMATION: Oligonucleotide as a primer having NNS
      sequences (for mutating the amino acid)
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (67)..(68)
<223> OTHER INFORMATION: n is a, c, g, or t

<400> SEQUENCE: 83
gacatgcctg tagcccatgt tgtagcaaac cctcaagctg agggggcagct ccagtggnns    60 aacnnsnnsg ccaatgccct cctggcc                                         87

<210> SEQ ID NO 84
<211> LENGTH: 57
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (145)..(147)
<223> OTHER INFORMATION: Oligonucleotide as a primer having NNS
      sequences (for mutating the amino acid

<400> SEQUENCE: 84
cagggcaatg atcccaaagt agacctgccc snnsnnsnna aagtcgagat agtcggg            57

<210> SEQ ID NO 85
<211> LENGTH: 65
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Oligonucleotide as a 5'-terminal linker to
      insert the PCR-amplified DNA into a phagemid vector

<400> SEQUENCE: 85
cccagccggc catggccgtc agatcatctt ctcgaacccc gagtgacatg cctgtagccc        60
atgtt                                                                    65

<210> SEQ ID NO 86
<211> LENGTH: 62
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Oligonucleotide as a 3'-terminal linker to
      insert the PCR-amplified DNA into a phagemid vector

<400> SEQUENCE: 86
ggcaccggcg cacctgcggc cgcagatcca ccaccaccca gggcaatgat cccaaagtag        60
ac                                                                       62

<210> SEQ ID NO 87
<211> LENGTH: 87
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
```

```
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (84)..(99)
<223> OTHER INFORMATION: Oligonucleotide as an anti-sense primer having
      NNS sequences (for mutating amino acid residues)

<400> SEQUENCE: 87
ctggcagggg ctgcggatgg cagagaggag attgacgggs nnsnnsnnsn nsnnsnngat    60
gcggctgatg gtgtgggtga ggagcac                                       87

<210> SEQ ID NO 88
<211> LENGTH: 218
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Oligonucleotide as a 3'-terminal linker to
      insert the PCR-amplified DNA into a phagemid vector

<400> SEQUENCE: 88
ggcaccggcg cacctgcggc cgcagatcca ccaccaccca gggcaatgat cccaaagtag    60
acctgcccag actcggcaaa gtcgagatag tcgggccgat tgatctcagc gctgagtcgg   120
tcacccggct ccagctggaa gaccectccc agatagatgg gctcatacca ggggttggcc   180
tcagccccct ctggggtctc cctctggcag gggctgcg                           218

<210> SEQ ID NO 89
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Oligonucleotide as a 5'-terminal linker to
      insert the PCR-amplified DNA into an expression vector

<400> SEQUENCE: 89
tatacatatg gtcagatcat cttctcgaac cccgagtg                            38

<210> SEQ ID NO 90
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Oligonucleotide as a 3'-terminal linker to
      insert the PCR-amplified DNA into an expression vector

<400> SEQUENCE: 90
aaggatccct acagggcaat gatcccaaag tagac                               35
```

TUMOR NECROSIS FACTOR-ALPHA MUTANTS

TECHNICAL FIELD

The present invention relates to tumor necrosis factor (hereinafter, it is abbreviated as "TNF") mutant proteins, more particularly, to TNF antagonists or agonists specific to TNT-R1 or TNF-R2 as a TNF receptor; and TNF inhibitors or TNF preparations containing thereof as effective ingredients.

BACKGROUND ART

TNF has been expected for use as an antitumor agent because it exerts an extremely strong antitumor effect on various tumor cells. However, TNF has not yet been successfully utilized as a pharmaceutical because of its excess side effect on living bodies due to its cytotoxic activity. When TNF is endogenously produced in a patient with a cancer or infectious disease, it may induce an inflammatory response and sometimes become an aggravating factor for such conditions. Therefore, development of a method to control TNF actions has been desired. As a method to control TNF activity, there has been a method for neutralizing TNF activity by administering antibodies, which bind to TNF, to living bodies. Pharmaceuticals containing such antibodies as effective ingredients have been already established. However, the above method may have a risk of canceling all beneficial biophylactic activities of TNF.

One TNF receptor having a molecular weight of 55 kilo daltons (hereinafter, it is called "TNF-R1") and the other with 75 kilo daltons (hereinafter, it is called "TNF-R2") are generally known as TNF receptors. Van Ostade X., Tavernier J., Prange T., and Fiers W. reported in "Localization of the active site of human tumor necrosis factor (hTNF) by mutational analysis", *The ENMO Journal*, Vol. 10, No. 4, pp. 827-836, 1991, that alpha-type TNF (hereinafter, it is called "TNF-α") of human origin, which dose not bind to mouse TNF-R2 and exerts a different biological effect differing from mouse TNF-α capable of binding to the both TNF receptors. Therefore, TNF mutant proteins selectively binding to either TNF-R1 or TNF-R2 would be expected to exert a different effect from that of conventional TNFs.

In order to create the TNF mutant proteins selectively binding to either TNF-R1 or TNF-R2, i.e., a receptor-specific TNF mutant protein, Van Ostade X et al. examined the binding sites in TNF-α to TNF-R1 or TNF-R2 by the mutational analysis as described in the above literature. As a result, they disclosed that mutagenesis at positions 29 to 34, 86 and 146 (amino acid residue numbers from the N-terminal of the amino acid sequence of TNF-α) enabled to weaken the binding affinity for TNF-R2, while mutagenesis at positions 143 to 145 enabled to weaken the binding affinity for TNF-R1. Particularly, they disclosed that TNF-α mutant protein, where the 32nd arginine (R) from the N-terminal was replaced with tryptophan (W), and the 86th serine (S) from the N-terminal was replaced with threonine (T), was extremely weakened in binding affinity for TNF-R2 while retaining the one for TNF-R1. Referring to Japanese Patent Publication Nos. 256395/94 and 285997/95; Zhang X M, Weber I and Chen M J, "Site-directed mutational analysis of human tumor necrosis factor-alpha receptor binding site and structure-functional relationship", *Journal of Biological Chemistry*, Vol. 267, No. 33, pp. 24069-24075, 1992; and Loetscher H, Stueber D, Banner D, Mackay F and Lesslauer W, in "Human tumor necrosis factor alpha (TNF alpha) mutants with exclusive specificity for the 55-kDa or 75-kDa TNF receptor", *The Journal of Biological Chemistry*, Vol. 268, No. 35, pp. 26350-26357, 1993, mutagenesis at positions 29 to 34, 81 to 89, and 143 to 147 (amino acid residue numbers from the N-terminal of TNF-α) may be hopeful to impart the receptor specificity to TNF mutant proteins. Receptor-specific TNF-α mutant proteins, retaining TNF activity as agonists, were prepared in the above literatures and might be expected as a TNF preparation with a potential TNF medical effect.

While, if TNF antagonist, which is a TNF mutant protein having a weak or no TNF activity, selectively binds to either of the two TNF receptors, it enables to allow an endogenously produced TNF to selectively bind to the remaining TNF receptor. However, the above literatures disclosed no TNF mutant protein having antagonistic activity specific to either of the TNF receptors. Therefore, receptor-specific TNF antagonist has been desired to develop.

DISCLOSURE OF THE INVENTION

Under the above circumstances, the present invention has objects to provide TNF mutant proteins, particularly, TNF antagonists specific to TNF-R1 or TNF-R2, and TNF inhibitors containing it as an effective ingredient.

In order to obtain TNF antagonists specific to TNF receptor TNF-R1 or TNF-R2, the present inventors exhaustively created and screened TNF mutant proteins. As a result, they successfully obtained TNF mutant proteins having extremely weaker binding affinity for only TNF-R1 than that of wild-type TNF, or other TNF mutant proteins having extremely weaker binding affinity for only TNF-R2 than that of wild-type TNF. They confirmed that these TNF mutant proteins were TNF antagonists capable of antagonistically inhibiting that TNF binds to either of the TNF receptors, or TNF agonists capable of selectively binding to either of the TNF receptors and exhibiting a TNF like activity, and then accomplished this invention.

The present invention solves the above objects by providing TNF antagonists or TNF agonists specific to TNF-R1 or TNF-R2, and a TNF inhibitor containing it as an effective ingredient.

BEST MODE FOR CARRYING OUT THE INVENTION

The term "specific to TNF-R1" as referred to as in the present invention means that it has a remarkable binding affinity for TNF-R1 due to an extremely weak binding affinity for TNF-R2, and the term "specific to TNF-R2" means that it has a remarkable binding affinity for TNF-R2 due to an extremely weak binding affinity for TNF-R1. The term "TNF antagonist" as referred to as in the present invention means a protein capable of binding to TNF receptors but showing a weaker activity than that of wild-type TNF or no activity. The TNF antagonist of the present invention preferably has a binding affinity for either TNF-R1 or TNF-R2 as strong as possible, and a binding affinity for the other as weak as possible.

The antagonist specific to TNF-R1 or TNF-R2 of the present invention can be obtained by introducing NNS sequence ("N" means a base of "A", "T", "G" or "C", and "S" means a base of "G" or "C") into the desired position of a DNA encoding TNF-α comprising an amino acid sequence of SEQ ID NO:1 by usual PCR technique; and selecting clones having the desired property using phage display method. Lysine-replaced TNF mutants, where one or more lysine residues selected from the group consisting of the 11th, 65th, 90th, 98th, 112th and 128th lysine residues from the N-terminal of the amino acid sequence of SEQ ID NO:1 is/are deleted or replaced with other amino acid residue(s), preferably, those having any one of the amino acid sequences shown in parallel in nucleotide sequences of SEQ ID NOs:2 to 4, can be original of the antagonists as well as TNF-α (hereinafter, it is simply called "lysine-replaced mutant".). Concretely explaining, for the purpose of changing the binding affinity for TNF-R1 or TNF-R2, DNAs, where the codons corresponding to the 29th, 31st, 32nd, 145th, 146th and 147th amino acid residues (SEQ ID NO:5), or to the 84th, 85th, 86th, 87th, 88th and 89th amino acid residues (SEQ ID NO:7) from the N-terminal of the amino acid sequence of SEQ ID NO:1 or shown in parallel in the nucleotide sequence of SEQ ID NOs:2 to 4 are replaced with NNS (SEQ ID NOs: 6 or 8), are produced by usual oligo DNA synthetic technique, PCR technique, DNA ligation technique, etc., to introduce random amino acid residues into the above amino acid sequences at the above positions. The obtained DNAs are introduced into phagemid vectors to prepare a phage library. After expressing proteins, phage clones binding to TNF-R1 (a protein having the amino acid sequence, Accession No. M58286 registered at GENBANK) or TNF-R2 (a protein having the amino acid sequence, Accession No. M55994 registered at GENBANK) are selected by panning method using a detector based on surface plasmon resonance effect etc. The obtained clones are further examined for binding affinity for the remaining receptor (TNF-R2 or TNF-R1) to select clones having a different binding affinity for the two receptors, or having binding affinity reduced to a half, preferably a tenth, more preferably a thousandth in comparison with the original TNF-α or lysine replaced TNF, and most preferably below a detectable level. The selected clones are subjected to usual bioassay for measuring their biological activity using TNF-sensitive target cells such as HEp-2 cells (ATCC CCL-23) originated from a human laryngeal cancer and L-M cells (ATCC CCL-1.2) originated from a mouse connective tissue. As a result, phage clones having a weakened cytotoxic activity are selected, for example, those which have the cytotoxic activity reduced to a half, preferably a tenth, more preferably a thousandth, the most preferably below a detectable cytotoxic level.

The obtained TNF antagonists of the present invention have either of amino acid sequences where part or the whole of the amino acid residues selected from the group consisting of 29th, 31st, 32nd, 145th, 146th and 147th, or the group consisting of 84th to 89th from the N-terminal of TNF-α having the amino acid sequence of SEQ ID NO:1, or lysine-replaced TNF mutant proteins having the amino acid sequences shown in parallel in nucleotide sequences of SEQ ID NOs: 2 to 4 are replaced with other amino acid residues or stop codons. Because these TNF mutant proteins specifically bind to TNF-R1 or TNF-R2, and have a weaker activity than wild-type TNF or no activity, i.e., TNF antagonists specific to TNF-R1 or TNF-R2, they selectively bind to either TNF-R1 or TNF-R2, and inhibit endogenously produced TNF to bind to the selected receptor when administered to living bodies. Therefore, TNF antagonists of the present invention can control endogenous TNFs to exert the TNF activity mediated by either of the TNF receptors when administered in an excess amount to endogenous TNF.

Examples of the TNF antagonists specific to TNF-R1 of the present invention are TNF mutant proteins having an amino acid sequence where the 29th amino acid residue from the N-terminal of the amino acid sequence of SEQ ID NO:1 is replaced with arginine, histidine or serine; the 31st amino acid residue replaced with arginine, asparagine, glutamic acid, proline or serine; the 32nd amino acid residue replaced with histidine, methionine, threonine or tyrosine; the 145th amino acid residue replaced with alanine, asparagine, aspartic acid or serine; the 146th amino acid residue replaced with asparagine, glycine, methionine or serine; and the 147th amino acid residue replaced with alanine, asparagine, proline, threonine or stop codons; or the 84th amino acid residue from the N-terminal of the amino acid sequence of SEQ ID NO:1 is replaced with alanine, threonine, serine or glycine; the 85th amino acid residue replaced with proline, threonine or glycine; the 86th amino acid residue replaced with alanine, glycine, threonine or proline; the 87th amino acid residue replaced with tyrosine, isoleucine or histidine; the 88th amino acid residue replaced with glutamine, asparagine or serine; and the 89th amino acid residue replaced with arginine, histidine or glutamine; which are preferably illustrated with TNF mutant protein having either of the amino acid sequences of SEQ ID NOs: 9 to 13 or Nos: 19 to 22. Examples of the TNF antagonists specific to TNF-R2 of the present invention are TNF mutant proteins having an amino acid sequence where the 145th amino acid residue from the N-terminal of the amino acid sequence of SEQ ID NO:1 is replaced with alanine, lysine or arginine; the 146th amino acid residue replaced with glutamic acid, asparagine, aspartic acid or threonine, or the 147th amino acid residue replaced with threonine or aspartic acid, which are preferably illustrated with TNF mutant protein having either of the amino acid sequences of SEQ ID NOs. 14 to 18.

After screening of the TNF antagonists of the present invention, TNF mutant proteins, specifically binding to TNF-R1 and having intact or slightly weakened TNF activity, were obtained. These proteins are expected to exert a different biological activity from that of wild-type TNF due to lack of the binding affinity for TNF-R2, and thought to act as a TNF agonist. Examples of such proteins are TNF mutant proteins having an amino acid sequence where the 29th amino acid residue from the N-terminal of the amino acid sequence of SEQ ID NO:1 is replaced with leucine, glutamine, threonine or lysine; the 31st amino acid residue replaced with arginine, glycine, serine or alanine; the 32nd amino acid residue replaced with tryptophan, tyrosine, aspartic acid or glycine; the 146th amino acid residue replaced with glutamic acid, alanine or serine; the 147th amino acid residue replaced with serine, arginine or threonine; or the 84th amino acid residue from the N-terminal of the amino acid sequence of SEQ ID NO:1 is replaced with threonine, serine or asparagine; the 85th amino acid residue replaced with serine, lysine, proline, tyrosine, arginine, threonine, histidine, glutamic acid, aspartic acid or alanine; the 86th amino acid residue replaced with histidine, threonine, leucine, asparagine, alanine, valine, lysine, serine, glutamine, glycine, arginine or aspartic acid; the 88th amino acid residue replaced with serine, proline, threonine, asparagine, alanine, glycine, arginine or glutamine; and the 89th amino acid residue replaced with aspartic acid, histidine, lysine, glycine, serine, proline, alanine, glutamine, phenylalanine or arginine; which are illustrated with the TNF mutant proteins having either of the amino acid sequences of SEQ ID NO: 37 to 59.

The term "lysine-replaced TNF" as referred to as in the present invention means a TNF mutant protein prepared by the present inventors (reference to European Patent Publication No. EP1354893) for the purpose of conjugating TNF-α with a water-soluble polymer without reducing its biological activity, where one or more lysine residues selected from the group consisting of the 11th, 65th, 90th, 98th, 112th and 128th lysine residues from the N-terminal of the amino acid sequence of TNF-α are replaced with other amino acid residues or deleted. The lysine-replaced TNFs have an amino acid sequence shown in parallel in nucleotide sequences of SEQ ID NOs: 2 to 4, and shows the same level of TNF activity or more as that of TNF-α. They also show substantially the same level of binding affinity as that of TNF-α for TNF-R1 and TNF-R2. Therefore, the lysine-replaced TNFs having no or smaller numbers of lysine residues are advantageously used for conjugating TNF antagonist specific to TNF-R1 or TNF-R2 with a water-soluble polymer to make into a complex for use as a pharmaceutical. The TNF antagonists of the present invention having either of the amino acid sequences of SEQ ID NOs: 9 to 22, or the TNF antagonists of the present invention having either of the amino acid sequences of SEQ ID NOs: 37 to 59, which are created from the original lysine-replaced TNF, may be preferred examples for forming complexes with water-soluble polymers because they have no or only one lysine residue. In the case that the TNF mutant proteins of the present invention will not be intended to conjugate with water-soluble polymers, one or more, or all of the amino acid residues selected from the group consisting of the 11th, 65th, 90th, 98th, 112th and 128th amino acid residues from the N-terminal of the amino acid sequences of SEQ ID NOs: 9 to 22 and NOs: 37 to 59 can be made lysine residue(s) similarly as in wild-type TNF.

The TNF mutant proteins of the present invention can be produced according to usual gene technology using DNAs encoding them; for example, DNAs having either of the nucleotide sequences of SEQ ID NOs:23 to 36, or NOs: 60 to 82. In order to obtain a desired amount of a TNF mutant protein, a DNA encoding any one of the TNF mutant proteins of the present invention, if necessary amplified by PCR, is introduced into a plasmid vector for protein expression, and then introduced into a host such as *E. coli* for transforming. Clones capable of producing the objective protein are selected from the resulting transformants, and cultured. Usual protein purification methods such as dialysis, salting out, filtration, concentration, centrifuging, separatory sedimentation, gel filtration chromatography, ion exchange chromatography, reverse phased chromatography, affinity chromatography, chromatofocusing, gel electrophoresis and isoelectric focusing can be applied in order to collect the expressed protein from the extract of the cultured transformants, and if necessary the above methods can be used in appropriate combination.

The TNF mutant proteins of the present invention can be artificially conjugated with a water-soluble polymer in order to improve their stability in living bodies. The water-soluble polymer used in the present invention can be preferably chosen from substantially water-soluble substances, particularly, non-toxic and hardly antigenic non-proteinaceous substances. Examples of such substances are synthetic polymers such as monopolymers including polyvinyl alcohol, polyethylene glycol, polyvinyl pyrrolidone and polypropylene glycol; copolymers of ethylene glycol with vinyl alcohol or propylene glycol, and derivatives thereof; and natural polymers such as elsinan, dextran, hydroxyethyl cellulose, pullulan and methyl cellulose. Particularly, monopolymers of polyethylene glycol, copolymers of polyethylene glycol with other water-soluble polymer and derivatives thereof are preferably chosen because they are easily obtainable as a preparation with a uniform molecular weight. The water-soluble polymer can be chosen from those in the range of average molecular weight of, usually 500 to 100,000 daltons, preferably 1,000 to 50,000 daltons. When the water-soluble polymer having a uniform molecular weight is required, it can be fractionated by usual method such as separatory sedimentation and gel filtration chromatography before subjected to the reaction for conjugating with proteins. A water-soluble polymer in a branched or straight form can be used, particularly, the former is preferable in view of steric hindrance. Varying depending on the kind of water-soluble polymer and the final use of the complex, when the molecular weight of the water-soluble polymer is below the above range, the resulting complex may not be satisfactorily improved on the kinetics in living bodies. While, when the molecular weight of the water-soluble polymer is over the above range, the resulting complex may be so excessively weakened in its physiological activity as to be useless for pharmaceuticals.

In order to conjugate TNF mutant proteins with a water-soluble polymer, the proteins are reacted with the water-soluble polymer pre-activated with an agent capable of forming a covalent bond by specifically reacting with a free amino group(s), or bridged with a water-soluble polymer using a polyfunctional agent having active groups capable of specifically reacting with a free amino group. Such reaction can be carried out according to the method described in International Patent Publication WO 95/13090. Usual method in the art such as ester-binding method and amide-binding method, disclosed in Japanese Patent Publication No. 289522/87, can also be used. The bond formed between the protein part and the water-soluble polymer part is preferably made according to the amide binding method capable of forming a stable covalent bond.

Varying depending on the reaction method used, the ratio of protein(s) and water-soluble polymer(s) employed in the initiation of reaction is increased or decreased within the range of 1:0.1 to 1:100, preferably 1:0.5 to 1:50, and more preferably 1:1 to 1:10, in a molar ratio. In general, when the ratio is below the above range, the proteins tend to easily bind each other; while when the ratio is over the above range, the water-soluble polymers become to easily bind each other. In any case, since the ratio outside the above preferable range will lower the reaction rate of the protein(s) and the polymer(s) and decrease the purification efficiency of the reaction product, the ratio should preferably be increased or decreased within the above-identified range. The reaction temperature, pH, and time are set so as not to inactivate and decompose the protein(s) and to minimize undesirable side reactions: The reaction temperature is set to 0-100° C., preferably 20-40° C.; the reaction pH is set to 0.1-12, preferably 5-9; and the time is set to one that terminates the reaction within 0.1-50 hours, preferably within 10 hours. The complexes of TNF mutant proteins with water-soluble polymers thus obtained can be purified by similar methods as used in purifying the mutant proteins, and optionally further treated with concentration, salting out, centrifugation, lyophilization, etc., into products in a liquid or solid form, depending on final use.

The TNF mutant proteins or the complexes thereof with the water-soluble polymers of the present invention are greatly useful as a TNF inhibitor or TNF preparation for treating and/or preventing susceptive diseases thereof, or alleviating symptoms such as inflammation. The term "susceptive diseases" as referred to as in the present invention means diseases in general which can be treated, prevented or alleviated by the administration of the TNF inhibitor or TNF preparation with or without other medicaments. Concretely, it is illustrated with various diseases caused or accompanied by overexpression of endogenous TNF or excessive administration of TNF, or effectively treated by antitumor activity of TNF; solid tumors such as colonic cancer, rectal cancer, gastric cancer, thyroid carcinoma, cancer of the tongue, bladder carcinoma, choriocarcinoma, hepatoma, carcinoma uteri, cancer of pharynx, lung cancer, breast cancer, malignant melanoma, neuroblastoma, pyo-ovarium, testicular tumor, osteosarcoma, pancreatic cancer, hypernephroma, goiter, brain tumor, malignant melanoma, and mycosis fungoides; hematopoietic tumors such as leukemia and lymphoma; autoimmune diseases such as ulcerative colitis, Crohn's disease, rheumatoid arthritis, allergy and psoriasis; and others such as cachexia, chronic and acute inflammation, arthritis, septicemic disease, disseminated intravascular coagulation, transplantation rejection, graft versus host disease, infection, apoplexy, ischemia, acute dyspnea, restenosis, encephalopathy, AIDS, SARS, bone disease, atherosclerosis, Kawasaki disease, Behcet's disease, systemic lupus erythematosus, multiple organ failure, malaria, meningitis, fulminant hepatitis, Bowel disease, and Alzheimer disease. Thus, the TNF inhibitor or the TNF preparation of the present invention has a variety of uses as pharmaceuticals for treating and/or preventing the above diseases, or alleviating symptoms such as inflammation.

When used in combination with TNF, the TNF antagonist of the present invention selectively exerts a similar action to that of the TNF agonist of the present invention, i.e., TNF activity mediated by TNF-R1 or TNF-R2. Such TNF is illustrated with TNF-α, TNF-β, mutant proteins thereof, or complexes thereof with water-soluble polymers. Varying the condition of patients, the ratio of TNF antagonist of the present invention to TNF can be freely decided; the amount of the TNF antagonist specific to TNF-R1 or TNF-R2 is 100,000 times or more, preferably 500,000 times or more to TNF in a molar ratio in order to substantially inhibit the exertion of TNF activity mediated by either of the receptors. Even if the TNF antagonists are below the above molar ratio, they can partially inhibit TNF activity. Therefore, the TNF antagonists can be expected to exert unusual TNF activity or lowered in side effect of TNF. Thus, the ratio of TNF antagonist and TNF is 1 to 1,000,000 times, preferably 10 to 1,000,000 times, more preferably 100 to 1,000,000 times in a molar ratio.

Varying depending on the types and the symptoms of susceptive diseases to be treated, the agent for susceptive diseases of the present invention is prepared to facilitate the administration of at least 0.25 ng/kg body weight per shot, preferably 2.5 ng to 400 mg/kg body weight per shot of the physiologically active complex while varying the dose level depending on the administration route; and is prepared into an extract, elixir, lower airway inhalation, capsule, granule, ophthalmic sustained-release-drug, pill, ophthalmic ointment, cataplasm for tunica mucosa oris, suspension, emulsion, plaster, suppository, powder, tablet, syrup, dipping agent, decoction, injection, intravenous fluid preparation, tincture, eyedrop, eardrop, nasal drop, troche, ointment, cataplasm, aromatic water, nasal nebulas, liniment, limonade, fluidextract, lotion, etc.

In order to determine the application of the TNF inhibitor or TNF preparation of the present invention and to estimate a proper dose, measuring the blood level of TNF and soluble TNF receptor (TNF-R1 and TNF-R2) or counting the number of TNF receptor on cell surface in the diseased tissues by usual enzyme immunoassay, flow cytometry or binding assay is meaningfully applied to patients.

The TNF inhibitor or TNF preparation of the present invention includes those in a dose unit form, which contain, for example, an amount equal to a single dose or an integral multiple dose of the single dose (up to four times), or to a division of the single dose thereof (up to 1/40 time); and which are in the form of a physically separated systematic agent suitable for administration. Examples of such are capsules; granules, pills, suppositories, powders, tablets, injections, intravenous fluid preparations and cataplasms.

In addition to the TNF mutant proteins of the present invention as the effective ingredient, appropriate agents such as excipients, ointment bases, dissolving agents, corrigents, flavors, colors, and emulsifiers, which are commonly used in preparing medicaments, can be freely incorporated into the TNF inhibitor or TNF preparation of the present invention. Within the scope of the object of the present invention, the TNF mutant proteins of the present invention can be used together with one or more other agents as other effective ingredient; for example, external dermal agents such as external dermal sterilizing and pasteurizing agents, wound protecting agents, and antiphlogistics; vitamin preparations such as vitamin A preparations, vitamin B preparations, vitamin C preparations, vitamin D preparations, vitamin E preparations, and vitamin K preparations; calcium preparations; mineral preparations; saccharide preparations; organic acid preparations; protein and amino acid preparations; revitalizers such as organ preparations; chlorophyll preparations; cell activating preparations such as dye preparations; antitumor agents such as alkylating agents, antimetabolites, antitumor antibiotics preparations, and antitumor plant-ingredient preparations; allergic agents such as antihistamines; chemotherapeutics such as antituberculosis drugs, synthetic antimicrobiral agents, and antiviral agents; and others such as hormone preparations, antibiotic preparations, and biological preparations.

The TNF inhibitor or TNF preparation of the present invention can be used as adjuvants in combination with antitumor drugs such as actinomycin D, aceglatone, ifosfamide, ubenimex, etoposide, enocitabin, aclarubicin hydrochloride, idarubicin hydrochloride, irinotecan hydrochloride, epirubicin hydrochloride, gemcitabine hydrochloride, daunorubicin hydrochloride, doxorubicin hydrochloride, nitrogen mustard-N-oxide hydrochloride, nimustine hydrochloride, pirarubicin hydrochloride, fadrozole hydrochloride hydrate, bleomycin hydrochloride, procarbazine hydrochloride, mitoxantrone hydrochloride, carboquone, carboplatin, carmofur, tamoxifen citrate, toremifene citrate, krestin, medroxyprogesterone acetate, cyclophosphamide, cisplatin, schizophyllan, cytarabine, cytarabine ocfosfate, zinostantin stimalamer, vinonelbin ditartrate, sobuzoxane, dacarbazine, thiotepa, tegafur, tegafur uracil, tegafur gimesutat otastat potassium, doxifluridine, docetaxel hydrate, toretinoin, neocarzinostatin, nedaplatin, paclitaxel, bicalutamido, picibanyl, hydroxycarbamide, busulfan, fluorouracil, flutamido, pentostatin, porfimer sodium, mitomycin C, mitobronitol, methotrexate, mercaptopurine, 6-mercaptopurine riboside, bleomycin sulfate, vincristine sulfate, vindesine sulfate, vinblastine sulfate, peplomycin sulfate, and lentinan. If the TNF inhibitor or TNF preparation is used in combination with cytokines such as interferons and interleukins or hormones such as insulin, or antibodies thereof, binding proteins thereof, agonists thereof, antagonists thereof, inhibitors thereof, or soluble receptor thereof, such combinations may easily exert so synergistic effect that the single uses thereof never attains.

The TNF inhibitor or TNF preparation of the present invention exerts therapeutic or prophylactic effects on susceptive diseases when administered orally and parenterally. Depending on the types and symptoms of susceptive diseases, the TNF antagonist or TNF agonist of the present invention is used in an oral administration, or in a parenteral administration by injection or intravenous drip, such as intradermal administration, subcutaneous administration, intramuscular administration, intravenous administration, intranasal administration, rectal administration and intraperitoneal administration, to a subject at a dose of 0.01 to 1,000 μg/day/kg body weight, preferably 0.1 to 100 μg/day/kg body weight, where the dose is optionally divided into several portions and the administration frequency is one to seven shots per week for one week to one year, as the symptoms of the patients and the progress after the administration are being observed. The complex of TNF mutant proteins of the present invention with water-soluble polymers is stable and hardly decomposed by protease in the blood, and stays significantly longer period in living bodies than TNF-α or TNF mutant proteins; some administration routes can attain ten times longer or more. Therefore, the complex gives a profit enabling to significantly minimize the dose when it is used for the same susceptive disease though the same administration route.

The following Experiments explain the present invention in detail.

Experiment 1

Preparing DNA Library Encoding TNF Mutant Proteins and Screening

According to usual method, a DNA encoding lysine-replaced human TNF (SEQ ID NO:2) disclosed in Example 2 in European Patent Publication No. EP1354893, i.e., a protein where the 11th, 65th, 90th, 98th, 112th and 128th lysine residues of the amino acid sequence of TNF-α had been replaced with methionine, serine, proline, arginine, asparagine and proline respectively was subjected as a template to usual PCR method using oligonucleotide primers represented by SEQ ID NOs:83 and 84 as primers. The resulting PCR product was further subjected as a template to usual PCR method using oligonucleotide primers represented by SEQ ID NOs:85 and 86 to obtain a DNA (SEQ ID NO:6) encoding TNF mutant proteins represented by SEQ ID NO:5 where the 29th, 31st, 32nd, 145th, 146th and 147th amino acid residues from the N-terminal were replaced with random amino resides. According to the same manner, the DNA encoding lysine-replaced human TNF (SEQ ID NO:2) was subjected as a template to usual PCR method using oligonucleotide primers represented by SEQ ID NOs:85 and 87. The resulting PCR product was further subjected as a template to usual PCR method using oligonucleotide primer represented by SEQ ID NO:88 to obtain DNA (SEQ ID NO:8) encoding proteins of SEQ ID NO:7 where the 84th to 89th amino acid residues were replaced with random amino resides.

According to usual manner, the resulting DNAs were introduced into a phagemid vector pCANTAB 5E (manufactured by Amersham Biosciences Corporation) to obtain a phagemid library which was expressing a TNF mutant protein where the 29th, 31st, 32nd, 145th, 146th and 147th amino acid residues from the N-terminal or the 84th to 89th amino acid residues from the N-terminal were replaced with random amino acid residues. The resulting library was subjected to panning method three times using a commercialized detector based on surface plasmon resonance effect (product name "BIACORE 2000", commercialized by BIACORE Corporation) equipped with a sensor tip conjugated with TNF-R1 (a protein having the amino acid sequence, Accession No. M58286 registered at GENBANK) to obtain phage clones binding to TNF-R1, and according to the same method using the detector equipped with a sensor tip conjugated with TNF-R2 (a protein having the amino acid sequence, Accession No. M55994 registered at GENBANK) to obtain phage clones binding to TNF-R2.

Using the above detector based on surface plasmon resonance effect again, the resulting clones binding to TNF-R1 (or TNF-R2) were subjected to the remaining sensor tip conjugated with TNF-R2 (or TNF-R1) to measure receptor binding affinity and select clones having a variation of receptor binding affinity. DNAs prepared from the selected clones were subjected to usual PCR method using oligonucleotide primers represented by SEQ ID NO:89 (containing restriction enzyme NdeI site, start codon and 5'-terminal nucleotide sequence of the TNF mutant protein) and 90 (containing restriction enzyme BamHI site, stop codon and 3'-terminal nucleotide sequence of the TNF mutant protein) to amplify the primer specific DNA. The resulting DNAs were digested with restrict enzymes NdeI and BamHI to obtain DNA fragments. The resulting DNA fragments were introduced into a plasmid vector containing T7 promoter region, T7 terminator region, ampicillin resistant gene region and ColE1/Ori region (product name "pET-3a", manufactured by "Novagen®" (EMD Biosciences, Inc.)) at the position of the above restriction sites. The resulting plasmid was introduced into *E. coli* BL21DE3 strain to obtain a transformed *E. coli* for producing the TNF mutant proteins. The obtained transformed *E. coli* was cultured according to usual method and centrifuged to collect *E. coli* pellet. The resulting pellet was washed twice with TES buffer (pH 8.0) (20 mM Tris-HCl, 10 mM ethylene diamine tetraacetic acid and 0.5 M sodium chloride) and admixed with TES buffer (pH 8.0) containing 0.2 mg/ml lysozyme. The resulting suspension was sonicated according to usual manner, and centrifuged to collect a precipitate containing the produced TNF mutant protein. The resulting precipitate was treated three times in a manner of admixing with TES buffer containing 1 (w/w) % Triton X-100, removed from supernatant by centrifuging, admixed with 50 mM Tris-HCl (pH 7.0) containing 8 M guanidine hydrochloride and 50 mM dithiothreitol, with stirring for 16 hours at ambient temperature under shielded condition, and centrifuged to collect a supernatant. The resulting supernatant was gently admixed with 100 time volumes of a aqueous solution containing 1 M Tris, 0.9 (w/v) % sodium chloride, 0.4 M L-arginine chloride, 2.5 mM reduced glutathione, 0.5 mM oxidized glutathione and 0.05 (w/v) % Tween 20, and kept at 4° C. for 16 hours. The resulting reaction mixtures were admixed with four fold volumes of phosphate buffer (pH 7.2) containing 0.1 (w/v) % bovine serum albumin, adjusted to pH 6.5 to 7.5, and purified by "Q-Sepharose" (manufactured by Pharmacia Co.), "Mono Q HR5/5" (manufactured by Pharmacia Co.), "Superrose 12 HR 10/30" (manufactured by Pharmacia Co.) and/or anti-TNF-α antibody column chromatography in turn according to usual manner.

The obtained TNF mutant proteins were subjected to usual bioassay using HEp-2 cells or L-M cells as target cells to examine their cytotoxicity. While, DNAs of these clones were subjected to usual DNA sequence method to determine their nucleotide sequences at the mutational positions. Based on the result, the amino acid residues or stop codons introduced by mutagenesis were confirmed. Judgment of cytotoxicity and binding affinity for receptors was conducted as follows using a recombinant TNF-α as a control produced from *E. coli* by a similar method as used in the above.

"4": Being improved by two times or more than that of the binding affinity or cytotoxicity of the recombinant TNF-α;

"3": Being substantially the same level as that of the binding affinity or cytotoxicity of the recombinant TNF-α (0.5 to 2 times);

"2": Being weakened to 0.5 to 0.1 time than that of the binding affinity or cytotoxicity of the recombinant TNF-α;

"1": Being weakened to 0.001 to 0.1 time than that of the binding affinity or cytotoxicity of the recombinant TNF-α;

"0": Being weakened to 0.001 or less than that of the binding affinity or cytotoxicity of the recombinant TNF-α;

"-": Being not measured.

The result is shown in Table 1 (TNF mutants where the 29th, 31st, 32nd, 145th, 146th and 147th amino acid residues are replaced.) and Table 2 (TNF mutants where the 84th to 89th amino acid residues are replaced.).

TABLE 1

| Clone No. | Bioassay | | Receptor binding affinity | | Mutational positions, amino acid residues introduced by mutagenesis, and their codons | | | | | | Note |
|---|---|---|---|---|---|

TABLE 2-continued

| Clone No. | Bioassay HEp-2 | Bioassay L-M | Receptor TNF-R1 | Receptor TNF-R2 | 84 | 85 | 86 | 87 | 88 | 89 | Note |
|---|---|---|---|---|---|---|---|---|---|---|---|
| 17 | 4 | 4 | 3 | 1 | Ser tcg | Lys aag | Thr acc | Tyr tac | Thr acc | His cac | SEQ ID NO: 42<br>SEQ ID NO: 65 |
| 18 | 4 | 4 | 4 | 1 | Ser tcc | Pro ccc | Leu ctg | Tyr tac | Pro ccc | Lys aag | SEQ ID NO: 43<br>SEQ ID NO: 66 |
| 19 | 4 | 4 | 4 | 1 | Ser tcc | Tyr acc | Asn aac | Tyr tac | Asn aac | Gly ggc | SEQ ID NO: 44<br>SEQ ID NO: 67 |
| 20 | 3 | 4 | 3 | 2 | Ser tcc | Ser agc | Ala gcg | Tyr tac | Ala gcg | Ser agc | SEQ ID NO: 45<br>SEQ ID NO: 68 |
| 21 | 4 | 4 | 4 | 1 | Thr tcg | Ser tcg | Ala gcc | Tyr tac | Gly ggg | Pro ccg | SEQ ID NO: 46<br>SEQ ID NO: 69 |
| 22 | 4 | 4 | 3 | 1 | Ser tcg | Arg cgc | Val gtg | Tyr tac | Thr acc | Ala gcc | SEQ ID NO: 47<br>SEQ ID NO: 70 |
| 23 | 4 | 4 | 4 | 1 | Thr acg | Thr acg | Ala gcg | Tyr tac | Ser agc | Gly ggc | SEQ ID NO: 48<br>SEQ ID NO: 71 |
| 24 | 4 | 4 | 4 | 1 | Thr acg | His cac | Lys aag | Tyr tac | Pro ccg | Gln cag | SEQ ID NO: 49<br>SEQ ID NO: 72 |
| 25 | 4 | 3 | 4 | 1 | Ser agc | Lys aag | Thr acc | Tyr tac | Ser tcc | His cac | SEQ ID NO: 50<br>SEQ ID NO: 73 |
| 26 | 4 | 2 | 4 | 1 | Ser tcg | Ser tcc | His cac | Tyr tac | Arg agg | Phe ttc | SEQ ID NO: 51<br>SEQ ID NO: 74 |
| 27 | 3 | 4 | 3 | 2 | Thr acc | Pro ccc | Ala gcc | Tyr tac | Pro ccc | Arg cgg | SEQ ID NO: 52<br>SEQ ID NO: 75 |
| 28 | 3 | 3 | 3 | 1 | Thr acg | Lys aag | Ser tcc | Tyr tac | Ser tcc | Lys aag | SEQ ID NO: 53<br>SEQ ID NO: 76 |
| 29 | 4 | 4 | 3 | 1 | Thr acc | Glu gag | Gln cag | Tyr tac | Ser tcc | His cac | SEQ ID NO: 54<br>SEQ ID NO: 77 |
| 30 | 4 | 4 | 3 | 2 | Thr acg | Pro ccc | Gly cag | Tyr tac | Pro ccg | Ser tcc | SEQ ID NO: 55<br>SEQ ID NO: 78 |
| 31 | 4 | 4 | 4 | 3 | Ser agc | Lys aag | Thr acc | Tyr tac | Ser tcc | His cac | SEQ ID NO: 56<br>SEQ ID NO: 79 |
| 32 | 3 | 4 | 4 | 2 | Thr acg | Asp gac | Arg cgc | Tyr tac | Ser agc | Ser agc | SEQ ID NO: 57<br>SEQ ID NO: 80 |
| 33 | 3 | 3 | 4 | 1 | Asn aac | His cac | Arg agg | Tyr tac | Gln cag | Asp gac | SEQ ID NO: 58<br>SEQ ID NO: 81 |
| 34 | 4 | 3 | 3 | 2 | Ser tcc | Ala gcg | Asp gac | Tyr tac | Pro ccc | His cac | SEQ ID NO: 59<br>SEQ ID NO: 82 |
| 35 | 0 | 0 | 4 | 0 | Thr acc | Pro ccc | Ala gcc | Ile atc | Asn aac | Arg cgg | SEQ ID NO: 19<br>SEQ ID NO: 33 |
| 36 | 1 | 1 | 3 | 1 | Ala gcg | Pro ccc | Gly ggc | Tyr tac | Ser tcc | His cac | SEQ ID NO: 20<br>SEQ ID NO: 34 |
| 37 | 1 | 1 | 3 | 1 | Ser agc | Thr acc | Thr acc | His cac | Asn aac | Gln cag | SEQ ID NO: 21<br>SEQ ID NO: 35 |
| 38 | 1 | 1 | 3 | 1 | Gly ggc | Gly ggc | Pro ccg | Tyr tac | Gln cag | Arg cgg | SEQ ID NO: 22 |

As shown in Table 1, both TNF-α as a control and the lysine-replaced TNF demonstrated substantially the same level of cytotoxicity and binding affinity for the TNF receptors. Regarding TNF mutant proteins created from the original lysine-replaced TNF, the TNF mutant proteins of clone Nos. 1 to 4 had a substantially the same level of binding affinity for TNF-R1 but a weaker affinity for TNF-R2, and showed a cytotoxic activity by bioassay using HEp-2 cells and L-M cells. While, the TNF mutant proteins of clone Nos. 5 to 9 had substantially the same or less binding affinity for TNF-R1 but an extremely weaker affinity for TNF-R2, and showed an extremely weakened cytotoxic activity by bioassay using HEp-2 cells and L-M cells. As a result, all of these clones were considered TNF mutant proteins specific to TNF-R1; TNF mutant proteins of clone Nos. 1 to 4 were revealed to be TNF agonists specific to TNF-R1, and TNF mutant proteins of clone Nos. 5 to 9 were revealed to be TNF antagonists specific to TNF-R1. TNF mutant proteins of clone Nos. 10 to 14 had substantially the same or more binding affinity for TNF-R2 than that of recombinant TNF-α as a control but an extremely weaker affinity for TNF-R1, and showed an extremely weakened cytotoxicity by bioassay using HEp-2 cells and L-M cells. As a result, the TNF mutant proteins of clone Nos. 10 to 14 were revealed to be TNF antagonists specific to TNF-R2.

As shown in Table 2, when compared with the lysine-replaced TNF as a control, TNF mutant proteins of clone Nos. 16 to 34 had substantially the same or more binding affinity for TNF-R1 but the same or weaker affinity for TNF-R2, and showed substantially the same cytotoxicity when determined by bioassay using HEp-2 cells and L-M cells. While TNF mutant proteins of clone Nos. 35 to 38 had substantially the same binding affinity for TNF-R1 but an extremely weaker affinity for TNF-R2, and showed an extremely weakened cytotoxicity. As a result, all of these clones were considered TNF mutant proteins specific to TNF-R1: TNF mutant proteins of clone Nos. 16 to 34 were revealed to be TNF agonists specific to TNF-R1, and TNF mutant proteins of clone Nos. 35 to 38 were revealed to be TNF antagonists specific to TNF-R1.

Experiment 2

Antagonistic TNF Inhibitory Activity

The above TNF antagonists of clone Nos. 35 to 38 were examined for antagonistic inhibitory activity in detail. Viability (the smaller value means the stronger TNF cytotoxic activity) of HEp-2 cells expressing only TNF-R1 on the cell surface or L-M cells expressing both of TNF-R1 and TNF-R2 (expressing TNF-R1 less than HEp-2) was measured by using a culture medium containing 10 ng/ml of a recombinant human TNF-α produced according to usual gene technology and TNF antagonist at the concentration shown in the following Table 3.

TABLE 3

| TNF antagonist | | TNF-α | Viability (%) | |
|---|---|---|---|---|
| | (ng/ml) | (ng/ml) | HEp-2 | L-M |
| | 0 | 10 | 9 | 17 |
| Clone No. 35 | 1,000 | 10 | 10 | 43 |
| | 10,000 | 10 | 18 | 58 |
| | 100,000 | 10 | 86 | 61 |
| | 500,000 | 10 | 103 | 64 |
| Clone No. 36 | 1,000 | 10 | 12 | 43 |
| | 10,000 | 10 | 13 | 54 |
| | 100,000 | 10 | 38 | 63 |
| | 500,000 | 10 | 74 | 59 |
| Clone No. 37 | 1,000 | 10 | 11 | 42 |
| | 10,000 | 10 | 18 | 51 |
| | 100,000 | 10 | 43 | 59 |
| | 500,000 | 10 | 75 | 72 |

TABLE 3-continued

| TNF antagonist | | TNF-α | Viability (%) | |
|---|---|---|---|---|
| | (ng/ml) | (ng/ml) | HEp-2 | L-M |
| Clone No. 38 | 1,000 | 10 | 11 | 42 |
| | 10,000 | 10 | 22 | 47 |
| | 100,000 | 10 | 72 | 58 |
| | 500,000 | 10 | 95 | 70 |

As shown in Table 3, in the presence of 10 ng/ml of a recombinant human TNF-α showing a strong cytotoxic activity, the addition of the TNF antagonist of each clone applied in this experiment increased viability of HEp-2 cells up to 86%, 38%, 43% or 72% from 9% at a concentration of 100,000 ng/ml or more, and partially cancelled the cytotoxic activity of recombinant TNF-α. Further, the addition of each TNF antagonist at a concentration of 500,000 ng/ml increased the viability up to 103%, 74%, 75% or 95%, and almost cancelled the cytotoxic activity of the TNF-α. While, the addition of the TNF antagonists increased viability of L-M cells up to 43%, 43%, 51% or 47% from 17% at a concentration of 1,000 ng/ml, but recovered the viability up to only 64%, 59%, 72% or 70% even at a concentration of 500,000 ng/ml. As a result, in order to allow the TNF antagonists of clone Nos. 35 to 38 to cancel the TNF activity against HEp-2 cells which express only TNF-R1 abundantly, the TNF antagonists might be required at a relatively-high concentration. They could perfectly cancel the TNF activity because HEp-2 cells do not express TNF-R2. In contrast, the TNF antagonists could easily cancel TNF activity mediated by TNF-R1 against L-M cells expressing both TNF-R1 and TNF-R2 because L-M cells express TNF-R1 in a low level. However, it was considered that the TNF antagonists could be anticipated to imperfectly cancel the TNF activity even at a high concentration because they were incapable of canceling TNF activity mediated by TNF-R2. Therefore, this result shows that the TNF antagonists of the present invention have TNF-R1 specificity.

Experiment 3

Preparation of a Complex of a TNF Mutant Protein and a Water-Soluble Polymer

Either of 14 TNF antagonists (clone Nos. 5 to 14, and Nos. 33 to 38) or 23 TNF agonists (clone Nos. 1 to 4, and Nos. 16 to 34) was dissolved in physiological phosphate buffered saline (pH 7.2) to give a concentration of 0.1 to 1 mg/ml and admixed with three fold of polyethylene glycol activated with monomethoxy N-succinimidylpropionate ("m-PAG-SPA", average molecular weight of 5,000 daltons) in a molar ratio to react at 37° C. for 30 minutes. ε-Aminocapronic acid (ten fold to the water-soluble polymer in a molar ratio) was added to the resulting reaction mixture and kept at rest for a time to terminate the reaction. The resulting mixture was subjected to HPLC fractionation using anion exchange chromatography column (product name "Mono S", manufactured by Amersham Bioscience Corporation) to remove unreacted polyethylene glycol from the proteins. Complexes of TNF mutant proteins of the present invention with a water-soluble polymer were finally obtained. The above 14 TNF-antagonistic complexes were similarly subjected to the antagonistic test using HEp-2 cells in Experiment 2 to measure TNF antagonistic inhibitory activity. As a result, they were determined to have an about 70% TNF antagonistic inhibitory activity of the corresponding each of the TNF antagonists which was not conjugated with polyethylene glycol.

Experiment 4

Acute Toxicity Test

According to usual manner, eight weeks aged male mice (body weight of 20 to 25 g) were percutaneously, orally or subabdominally (by injection) administered with any one of the 14 TNF antagonists (clone Nos. 5 to 14, and Nos. 35 to 38) or 23 TNF agonists (clone Nos. 1 to 4, and Nos. 16 to 34) prepared in Experiment 1, or any one of the complexes of the 14 TNF antagonists or 23 TNF agonists with polyethylene glycol prepared in Experiment 3. As a result, $LD_{50}$ of all of the TNF antagonists and the complexes thereof was above 100 mg/kg body weight by any route of administration. Therefore, the TNF mutant proteins and the complexes thereof with polyethylene glycol may be safely used as pharmaceuticals aiming to administer humans or domestic animals such as cows or as pharmaceutical ingredients.

The following examples explain the preferred embodiments of the present invention in detail.

Example 1

Liquid Preparation

Any one of the 14 TNF antagonists (clone Nos. 5 to 14, 35 to 38), 23 TNF agonists (clone Nos. 1 to 4, 16 to 34), prepared in Experiment 1, and 14 complexes of the TNF antagonists with polyethylene glycol, prepared in Experiment 3, was dissolved in physiological saline containing 1% (w/w) human serum albumin as a stabilizer to give a concentration of 100 mg/ml, and sterilized by usual microfiltration to obtain a liquid preparation.

The product is useful as an injection preparation, eye drop preparation, and nose drop preparation for treating or preventing susceptive diseases including malignant tumors, viral diseases, bacterial diseases, inflammatory diseases and immunnological diseases; and alleviating their symptoms.

Example 2

Liquid Preparation

Any one of the 14 TNF antagonists (clone Nos. 5 to 14, and Nos. 35 to 38), 23 TNF agonists (clone Nos. 1 to 4, and Nos. 16 to 34), prepared in Experiment 1, and 14 complexes of the TNF antagonists with polyethylene glycol, prepared in Experiment 3, was dissolved in physiological saline containing 1% (w/w) human serum albumin as a stabilizer to give a concentration of 10 mg/ml, admixed with 1 μg/ml of a recombinant human TNF-α, and sterilized by usual microfiltration to obtain a liquid preparation.

The product is useful as an injection preparation, eye drop preparation and nose drop preparation for treating or preventing susceptive diseases including malignant tumors, viral diseases, bacterial diseases, inflammatory diseases and immunnological diseases; and alleviating their symptoms.

Example 3

Dried Injection Preparation

One gram of any one of the 14 complexes of the TNF antagonists (clone Nos. 5 to 14, and Nos. 35 to 38) with polyethylene glycol, prepared in Experiment 3, and 0.1 mg of the physiologically active complex, prepared in Example 2 in European Patent Publication No. EP1354893 (i.e., a complex of lysine-replaced TNF having an amino acid sequence shown in parallel in nucleotide sequence of SEQ ID NO:2 with polyethylene glycol), were dissolved in 100 ml of physiological saline containing 1% (w/w) purified gelatin as a stabilizer, sterilized by usual microfiltraion, placed in vials by 1 ml, freeze-dried, and sealed to obtain a dried injection preparation.

The product is useful as an injection preparation, eye drop preparation and nose drop preparation for treating or preventing susceptive diseases including malignant tumors, viral diseases, bacterial diseases, inflammatory diseases and immunological diseases, and alleviating their symptoms.

Example 4

Ointment

Carboxyvinyl polymer (product name "HIVISWAKO", manufactured by WAKO PURE CHEMICALS Corporation) and pyrogen-free highly purified trehalose (product name "TREHA", manufactured by Hayashibara Inc.) were dissolved in sterilized distilled water to give concentrations of 1.4% (w/w) and 2.0% (w/w). Appropriate amount of any one of the 14 TNF antagonists (clone Nos. 5 to 14, and Nos. 35 to 38) and 23 TNF antagonist (clone Nos. 1 to 4, and Nos. 16 to 34), prepared in Experiment 1, was homogeneously admixed with the resulting mixture and adjusted to pH 7.2 to obtain a paste product containing about 10 μg/g of the TNF antagonist or TNF agonist.

The product having satisfactory extension property and stability is useful as an ointment for treating or preventing susceptive diseases such as malignant tumors, viral diseases, bacterial diseases, inflammatory diseases and immunological diseases.

Example 5

Tablet

An appropriate amount of any one of 14 complexes of TNF antagonists (clone Nos. 5 to 14, and Nos. 35 to 38) with polyethyleneglycol, prepared in Experiment 3, and a TNF antagonist (1/10,000 in a molar ratio to the complexes), which is a complex of lysine-replaced TNF having the amino acid sequence shown in parallel in the nucleotide sequence of SEQ ID NO:2, prepared in Example 2 in European Patent Publication No. EP1354893, were homogeneously admixed with anhydrous crystalline α-maltose powder (product name "FINETOSE", manufactured by Hayashibara Inc.). The resulting mixture was tableted by usual method to obtain a tablet (about 200 mg) containing about 10 mg of the physiologically active complex having TNF antagonist activity and about 1 μg of the physiologically active complex having TNF activity.

The product, having a satisfactory intake property and stability, is useful as a tablet for treating or preventing susceptive diseases such as malignant tumors, viral diseases, bacterial diseases, inflammatory diseases and immunological diseases.

INDUSTRIAL APPLICABILITY

As explained above, the TNF antagonists or the TNF inhibitors containing thereof as effective ingredients of the present invention have various uses in a pharmaceutical field, such as anti-tumor agents, anti-viral agents, anti-infective agents, agents for inflammatory diseases and agents for immunological diseases, because they selectively inhibit TNF actions mediated by TNF-R1 or TNF-R2. The TNF agonists capable of specifically binding to TNF-R1 can be expected to exert a different biological effect from that of wild-type TNF. The TNF mutant proteins of the present invention can be more advantageously used for pharmaceuticals because they can be more improved in stability in living bodies by conjugating with water-soluble polymers such as polyethylene glycol.

The invention claimed is:

1. A tumor necrosis factor mutant protein, which specifically binds to either the 55 kilodalton TNF-receptor (TNF R1) or the 75 kilodalton TNF receptor (TNF R2), wherein four or more amino acid residues selected from the group consisting of the 29th, 31st, 32nd, $84^{th}$ to $89^{th}$, 145th, 146th and 147th amino acid residues of the amino acid sequence of SEQ ID NO:1 are replaced with other amino acid residues.

2. The tumor necrosis factor mutant protein of claim 1, where the 29th amino acid residue of the amino acid sequence of SEQ ID NO:1 is replaced with arginine, histidine or serine; the 31st amino acid residue replaced with arginine, asparagine, glutamic acid, proline or serine; the 32nd amino acid residue replaced with histidine, methionine, threonine or tyrosine; the 145th amino acid residue replaced with alanine, asparagine, aspartic acid or serine; the 146th amino acid residue replaced with asparagine, glycine, methionine or serine; and the 147th amino acid residue replaced with alanine, asparagine, proline, threonine or a stop codon;

where the 145th amino acid residue is replaced with alanine, lysine or arginine; the 146th amino acid residue replaced with glutamic acid, asparagine, aspartic acid or threonine; and the 147th amino acid residue replaced with threonine or aspartic acid; or where the 84th amino acid residue is replaced with alanine, threonine, serine or glycine; the 85th amino acid residue replaced with proline, threonine or glycine; the 86th amino acid residue replaced with alanine, glycine, threonine or proline; the 87th amino acid residue replaced with tyrosine, isoleucine or histidine; the 88th amino acid residue replaced with glutamine, asparagine or serine; and the 89th amino acid residue replaced with arginine, histidine or glutamine.

3. The tumor necrosis factor mutant protein of claim 1, where the 29th amino acid residue of the amino acid sequence of SEQ ID NO:1 is replaced with leucine, glutamine, threonine or lysine; the 31st amino acid residue replaced with arginine, glycine, serine or alanine; the 32nd amino acid residue replaced with tryptophan, tyrosine, aspartic acid or glycine; the 146th amino acid residue replaced with glutamic acid, alanine or serine; and the 147th amino acid residue replaced with serine, arginine or threonine; or where the 84th amino acid residue is replaced with threonine, serine or asparagine, the 85th amino acid residue replaced with serine, lysine, proline, tryosine, arginine, threonine, histidine, glutamic acid, aspartic acid or alanine; the 86th amino acid reside replased with histidine, threonine, leucine, asparagine, alanine, valine, lysine, serine, glutamine, glycine, arginine or aspartic acid; the 88th amino acid residue replaced with serine, proline, threonine, asparagine, alanine, glycine, arginine or glutamine; and the 89th amino acid residue replaced with aspartic acid, histidine, lysine, glycine, serine, proline, alanine, glutamine, phenylalanine or arginine.

4. A tumor necrosis factor composition, which comprises the tumor necrosis factor mutant protein of claim 3 and a pharmaceutically acceptable carrier.

5. The tumor necrosis factor mutant protein of claim 1, which comprises either (i) the amino acid sequence selected from the group consisting of SEQ ID NOs:9 to 22, or (ii) the amino acid sequence, wherein one or more amino acid residues selected from the group consisting of the 11th, 65th, 90th, 98th, 112th and 128th amino acid residues of said amino acid sequence (i) are replaced with lysine residues.

6. The tumor necrosis factor mutant protein of claim 1, conjugated to a water-soluble polymer.

7. A tumor necrosis factor composition, which comprises the tumor necrosis factor mutant protein of claim 1 and a pharmaceutically acceptable carrier.

8. A tumor necrosis factor composition, which comprises the tumor necrosis factor mutant protein of claim 2 and a pharmaceutically acceptable carrier.

9. A tumor necrosis factor composition, which comprises the tumor necrosis factor mutant protein of claim 5 and a pharmaceutically acceptable carrier.

* * * * *